(12) United States Patent
Xie et al.

(10) Patent No.: US 11,925,579 B2
(45) Date of Patent: Mar. 12, 2024

(54) FLEXIBLE MICROFLUIDIC MESHWORK FOR GLAUCOMA SURGERY

(71) Applicants: BOARD OF REGENTS, THE UNIVERSITY OF TEXAS SYSTEM, Austin, TX (US); THE REGENTS OF THE UNIVERSITY OF CALIFORNIA, Oakland, CA (US)

(72) Inventors: Chong Xie, Austin, TX (US); Lan Luan, Austin, TX (US); Ying Han, Burlingame, CA (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 765 days.

(21) Appl. No.: 16/487,915

(22) PCT Filed: Feb. 22, 2018

(86) PCT No.: PCT/US2018/019106
§ 371 (c)(1),
(2) Date: Aug. 22, 2019

(87) PCT Pub. No.: WO2018/156687
PCT Pub. Date: Aug. 30, 2018

(65) Prior Publication Data
US 2019/0374384 A1 Dec. 12, 2019

Related U.S. Application Data

(60) Provisional application No. 62/462,132, filed on Feb. 22, 2017.

(51) Int. Cl.
*A61F 9/007* (2006.01)
*A61F 2/00* (2006.01)
*A61F 9/00* (2006.01)

(52) U.S. Cl.
CPC ........ *A61F 9/00781* (2013.01); *A61F 2/0063* (2013.01); *A61F 9/0017* (2013.01)

(58) Field of Classification Search
CPC ... A61F 9/00781; A61F 2/0063; A61F 9/0017
See application file for complete search history.

(56) References Cited

U.S. PATENT DOCUMENTS

| 8,632,489 B1 * | 1/2014 | Ahmed | A61F 9/00781 604/9 |
| 10,588,749 B2 * | 3/2020 | Sharp | B33Y 10/00 |

(Continued)

FOREIGN PATENT DOCUMENTS

| CN | 102427776 B * | 2/2016 | A61F 2/148 |
| WO | WO-2016197006 A1 * | 12/2016 | B33Y 80/00 |

OTHER PUBLICATIONS

The AGIS Investigators, "The Advanced Glaucoma Intervention Study (AGIS): 7. The relationship between control of Intraocular pressure and visual field deterioration", American Journal of Ophthalmology, vol. 130, No. 4, pp. 429-440.

(Continued)

*Primary Examiner* — Benjamin J Klein
*Assistant Examiner* — Kate Elizabeth Strachan
(74) *Attorney, Agent, or Firm* — Riverside Law LLP

(57) ABSTRACT

The invention provides for novel glaucoma surgical devices comprising a microfluidic meshwork. The meshwork comprises interconnected, cellular-dimensioned microfluidic channels. Excess fluid in the eye can be drained and diffused through the microfluidic channels. The meshwork is porous and highly flexible, affording mechanical compliance similar to that of eye tissue. The meshwork minimizes foreign body reactions to the implant, decreasing fibrosis and capsule formation.

19 Claims, 12 Drawing Sheets

(56) References Cited

U.S. PATENT DOCUMENTS

| | | | |
|---|---|---|---|
| 2004/0193095 A1 | 9/2004 | Shadduck | |
| 2005/0184003 A1 | 8/2005 | Rodgers | |
| 2006/0173397 A1* | 8/2006 | Tu | A61F 9/00781 604/8 |
| 2009/0287136 A1 | 11/2009 | Castillejos | |
| 2010/0249691 A1 | 9/2010 | Van Der Mooren | |
| 2011/0196281 A1* | 8/2011 | Lynch | A61M 25/007 604/9 |
| 2013/0261530 A1* | 10/2013 | Yalamanchili | F16K 15/031 604/9 |
| 2013/0274717 A1 | 10/2013 | Dunn | |
| 2014/0081194 A1* | 3/2014 | Burns | A61P 27/06 604/8 |
| 2016/0058615 A1* | 3/2016 | Camras | A61F 9/00781 604/9 |
| 2016/0302967 A1* | 10/2016 | Ahn | A61M 27/006 |
| 2017/0068018 A1* | 3/2017 | Qian | A61L 27/34 |
| 2018/0200185 A1* | 7/2018 | Labib | A61L 31/16 |
| 2020/0140439 A1* | 5/2020 | Rybtchinski | H10K 85/621 |

OTHER PUBLICATIONS

Thieme H et al., "Histopathologic Findings in Early Encapsulated Blebs of Young Patients Treated With the Ahmed Glaucoma Valve", Journal of Glaucoma, vol. 20, No. 4 (2011), pp. 246-251.

Turalba AV et al., "Hypertensive phase and early complications after Ahmed glaucoma valve implantation with Intraoperative subtenon triamcinolone acetonide", Clinical Ophthalmology, vol. 8 (2014), pp. 1311-1316.

Vajaranant TS et al., "The Changing Face of Primary Open-Angle Glaucoma in the United States: Demographic and Geographic Changes From 2011 to 2050", American Journal of Ophthalmology, vol. 154, No. 2 (2012), pp. 303-314.

Van de Velde S et al., "Modulation of wound healing in glaucoma surgery", Progress in Brain Research, vol. 221 (2015), pp. 319-340.

Wamsley S et al., "Results of the use of the Ex-PRESS miniature glaucoma implant in technically challenging, advanced glaucoma cases: a clinical pilot study", American Journal of Ophthalmology, vol. 138, No. 6 (2004), pp. 1049-1051.

Xie C et al., "Three-dimensional macroporous nanoelectronic networks as minimally invasive brain probes", Nature Materials, vol. 14, No. 12 (2015), pp. 1286-1292.

Yamanaka O et al., "Pathobiology of wound healing after glaucoma filtration surgery", BMC ophthalmology, vol. 15, No. 1 (2015), p. 157.

Yazdani S et al., "Adjunctive Mitomycin C or Amniotic Membrane Transplantation for Ahmed Glaucoma Valve Implantation: a Randomized Clinical Trial", Journal of Glaucoma, vol. 25, No. 5 (2016), pp. 415-421.

Alvarado JA et al., "Ahmed Valve Implantation with Adjunctive Mitomycin C and 5-Fluorouracil: Long-term Outcomes", American Journal of Ophthalmology, vol. 146, No. 2 (2008), pp. 276-284.

Anderson JM et al., "Foreign body reaction to biomaterials", Seminars in Immunology, vol. 20, No. 2 (2008), pp. 86-100.

Ayyala RS et al., "Comparison of Different Biomaterials for Glaucoma Drainage Devices", Archives of Ophthalmology, vol. 117, No. 2 (1999), pp. 233-236.

Ayyala RS et al., "Comparison of Different Biomaterials for Glaucoma Drainage DevicesPart 2", Archives of Ophthalmology, vol. 118, No. 8 (2000), pp. 1081-1084.

Bahler CK et al., "Second-generation trabecular meshwork bypass stent (iStent inject) increases outflow facility in cultured human anterior segments", American Journal of Ophthalmology, vol. 153, No. 6 (2012), pp. 1206-1213.

Brandão LM et al., "Update on Minimally Invasive Glaucoma Surgery (MIGS) and New Implants", Journal of Ophthalmology, vol. 2013 (2013), Article ID 705915.

Budenz DL et al., "Five-Year Treatment Outcomes in the Ahmed Baerveldt Comparison Study", Ophthalmology, vol. 122, No. 2 (2015), pp. 308-316.

Caprioli J et al., "Intraocular Pressure: Modulation as Treatment for Glaucoma", American Journal of Ophthalmology, vol. 152, No. 3 (2011), pp. 340-344.

Christakis PG et al., "The ahmed versus baerveldt study: Three-year treatment outcomes", Ophthalmology, vol. 120, No. 11 (2013), pp. 2232-2240.

Coleman, AL et al., "Practice patterns and treatment changes for open-angle glaucoma: the RiGOR study", Journal of Comparative Effectiveness Research, vol. 5, No. 1 (2015), pp. 79-85.

Collaborative Normal-Tension Glaucoma Study Group, Comparison of glaucomatous progression between untreated patients with normal-tension glaucoma and patients with therapeutically reduced intraocular pressures, American Journal of Ophthalmology, vol. 126, No. 4 (1996), 487-497.

Costa VP et al., "Efficacy and Safety of Adjunctive Mitomycin C during Ahmed Glaucoma Valve Implantation", Ophthalmology, vol. 111, No. 6 (2004), pp. 1071-1076.

Danesh-Meyer HV et al., "Cosmetically Significant Proptosis Following a Tube Shunt Procedure", Archives of Ophthalmology, vol. 120, No. 6 (2002), pp. 846-847.

DeCroos FC et al., "Expanded Polytetrafluoroethylene Membrane Alters Tissue Response to Implanted Ahmed Glaucoma Valve", Current Eye Research, vol. 34, No. 7 (2009), pp. 562-567.

Gedde SJ et al., "Evidence-based comparison of aqeous shunts", Current Opinion in Ophthalmology, vol. 24, No. 2 (2013), pp. 87-95.

Gedde SJ et al., "Three-year follow-up of the tube versus trabeculectomy study", American Journal of Ophthalmology, vol. 148, No. 5 (2009), pp. 670-684.

Gedde SJ et al., "Treatment Outcomes in the Tube Versus Trabeculectomy (TVT) Study After Five Years of Follow-up", American Journal of Ophthalmology, vol. 153, No. 5 (2012), pp. 789-803.

Gressel MG et al., "Trabeculectomy in young Patients", Ophthalmology, vol. 91, No. 10 (1984), pp. 1242-1246.

Hinkle DM et al., "A Comparison of the Polypropylene Plate Ahmed™ Glaucoma Valve to the Silicone Plate Ahmed™ Glaucoma Flexible Valve", European Journal of Ophthalmology, vol. 17, No. 5 (2007), pp. 696-701.

Hoeh H et al., "Early postoperative safety and surgical outcomes after implantation of a suprachoroidal micro-stent for the treatment of open-angle glaucoma concomitant with cataract surgery", Journal of Cataract and Refractive Surgery, vol. 39, No. 3 (2013), pp. 431-437.

Hunter KS et al., "Characterization of micro-invasive travecular bypass stents by ex vivo perfusion and computational low modeling", Clinical Opthalmology, vol. 8 (2014), pp. 499-506.

Ishida K et al., "Comparison of Polypropylene and Silicone Ahmed Glaucoma Valves", Ophthalmology, vol. 113, No. 8 (2006), pp. 1320-1326.

Iwao K et al., "Long-term outcomes and prognostic factors for trabeculectomy with mitomycin C in eyes with uveitic glaucoma: a retrospective cohort study", Journal of Glaucoma, vol. 23, No. 2 (2014), pp. 88-94.

Kim YG et al., "Level of Vascular Endothelial Growth Factor in Aqueous Humor and Surgical Results of Ahmed Glaucoma Valve Implantation in Patients With Neovascular Glaucoma", Journal of Glaucoma, vol. 18, No. 6 (2009), pp. 443-447.

Kurnaz E et al., "The effect of adjunctive Mitomycin C in Ahmed glaucoma valve implantation", European Journal of Ophthalmology, vol. 15, No. 1 (2005), pp. 27-31.

Lama PJ et al., "Antifibrotics and Wound Healing in Glaucoma Surgery," Survey of Ophthalmology, vol. 48, No. 3 (2003), pp. 314-346.

Law SK et al., "Comparison of Safety and Efficacy between Silicone and Polypropylene Ahmed Glaucoma Valves in Refractory Glaucoma", Ophthalmology, vol. 112, No. 9 (2005), pp. 1514-1520.

Lee JW et al., "Tissue Response to Implantated Ahmed Glaucoma Valve with Adjunctive Amniotic Membrane in Rabbit Eyes", Ophthalmic Research, vol. 51, No. 3 (2014), pp. 129-139.

Lewis RA, "Ab interno approach to the subconjunctival space using a collagen glaucoma stent", Journal of Cataract and Refractive Surgery, vol. 40, No. 8 (2014), pp. 1301-1306.

(56) References Cited

OTHER PUBLICATIONS

Liu J et al., "Multifunctional three-dimensional macroporous nanoelectronic networks for smart materials", Proceedings of the National Academy of Sciences, vol. 110, No. 17 (2013), pp. 6694-6699.
Liu J et al., "Syringe-injectable electronics", Nature Nanotechnology, vol. 10, No. 7 (2015), pp. 629-636.
Luan L et al., "Ultra-flexible nanoelectronic probes form reliable, glial scar free neural integration", Science Advances, vol. 3, No. 2 (2017), e1601966.
Minckler DS et al., "Clinical results with the Trabectome for treatment of open-angle glaucoma", Ophthalmology, vol. 112, No. 6 (2005), pp. 962-967.
Minckler DS et al., "Trabectome (trabeculectomy-internal approach): additional experience and extended follow-up", Transactions of the American Ophthalmological Society, vol. 106 (2008), pp. 149-159.
National Institute for Health and Care Excellence. NICE guidelines [CG85]. Glaucoma: Diagnosis and management of chronic open angle glaucoma and ocular hypertension, 2009.
Nouri-Mahdavi K et al., "Evaluation of the Hypertensive Phase After Insertion of the Ahmed Glaucoma Valve", American Journal of Ophthalmology, vol. 136, No. 6 (2003), pp. 1001-1008.
Nyska A et al., "Biocompatibility of the Ex-PRESS miniature glaucoma drainage implant", Journal of Glaucoma, vol. 12, No. 3 (2003), pp. 275-280.
Pakravan M et al., "Effect of Early Treatment with Aqueous Suppressants on Ahmed Glaucoma Valve Implantation Outcomes", Ophthalmology, vol. 121, No. 9 (2014), pp. 1693-1698.
Paschalis EI et al., "A Novel Implantable Glaucoma Valve Using Ferrofluid", PLoS One, vol. 8, No. 6 (2013), e67404.
Prum BE et al., "Primary Open-Angle Glaucoma Preferred Practice Pattern Guidelines", Ophthalmology, vol. 123, No. 1 (2016), pp. P41-P111.
Richter GM et al., "Minimally invasive glaucoma surgery: current status and future prospects", Clinical Ophthalmology, vol. 10 (2016), 189-206.
Saheb H et al., "Optical coherence tomography of the suprachoroid after CyPass Micro-Stent implantation for the treatment of open-angle glaucoma", The British Journal of Ophthalmology, vol. 98, No. 1 (2014), pp. 19-23.
Sahiner N et al., "Creation of a Drug-Coated Glaucoma Drainage Device Using Polymer Technology: In Vitro and In Vivo Studies", Archives of Ophthalmology, vol. 127, No. 4 (2009), pp. 448-453.
Schwartz, et al. "Glaucoma drainage implants: a critical comparison of types", Current Opinions in Ophthalmology, vol. 17, No. 2 (2006), pp. 181-189.
Susanna R et al., "Partial Tenon's capsule resection with adjunctive mitomycin C in Ahmed glaucoma valve implant surgery", The British Journal of Ophthalmology, vol. 87, No. 8, (2003), pp. 994-998.
Susanna R, "Partial Tenon's Capsule Resection with Adjunctive Mitomicyn C in Ahmed Glaucoma Valve Insertion", Investigative Ophthalmology & Visual Science, vol. 44, No. 13 (2003), p. 1181.
Takihara Y et al., "Trabeculectomy With Mitomycin for Open-Angle Glaucoma in Phakic vs Pseudophakic Eyes After Phacoemulsification", Archives of Ophthalmology, vol. 129, No. 2 (2011), pp. 152-157.
Tanimoto SA et al., "Options in pediatric glaucoma after angle surgery has failed", Current Opinion in Ophthalmology, vol. 17, No. 2 (2006), pp. 132-137.
Teixeira SH et al., "Silicone Ahmed Glaucoma Valve With and Without Intravitreal Triamcinolone Acetonide for Neovascular Glaucoma: Randomized Clinical Trial", Journal of Glaucoma, vol. 21, No. 5 (2012), pp. 342-348.
Tham, YC et al., "Global prevalence of glaucoma and projections of glaucoma burden through 2040: a systematic review and meta-analysis", Ophthalmology, vol. 121, No. 11 (2014), pp. 2081-2090.

\* cited by examiner

FLEXIBLE MICROFLUIDIC MESHWORK FOR GLAUCOMA SURGERY

CROSS-REFERENCE TO RELATED APPLICATIONS

This application is the U.S. national phase application filed under 35 U.S.C. § 371 claiming benefit to International Patent Application No. PCT/US18/19106 filed Feb. 22, 2018, which is entitled to priority under 35 U.S.C. § 119(e) to U.S. Provisional Patent Application No. 62/462,132, filed Feb. 22, 2017, the contents of which are each incorporated by reference herein in their entirety.

STATEMENT REGARDING FEDERALLY SPONSORED RESEARCH OR DEVELOPMENT

This invention was made with government support under Grant no. TR001872 awarded by the National Institutes of Health. The government has certain rights in the invention.

BACKGROUND OF THE INVENTION

Glaucoma is the leading cause of irreversible blindness in the world (Vajaranant T S et al., American journal of ophthalmology 154.2 (2012): 303-314). To date, controlling intraocular pressure (IOP) remains the primary treatment option (Caprioli J et al., American journal of ophthalmology 152.3 (2011): 340-344). Glaucoma surgery is commonly considered when glaucoma eye drops and laser therapies fail to lower IOP (Lama P J et al., Survey of ophthalmology 48.3 (2003): 314-346). The fundamental concept of glaucoma surgery is to artificially create an additional pathway for aqueous humor (AH) outflow, therefore lowering IOP.

Trabeculectomy, glaucoma drainage implants (GDIs) and minimally invasive glaucoma surgeries (MIGS) are the currently available surgical treatment for glaucoma. Trabeculectomy is the standard surgical approach to treat adult primary glaucoma, but its success in children and certain glaucoma populations is limited (Tanimoto S A et al., Current opinion in ophthalmology 17.2 (2006): 132-137; Gressel M G et al., Ophthalmology 91.10 (1984): 1242-1246; Iwao K et al., Journal of glaucoma 23.2 (2014): 88-94; Takihara Y et al., Archives of Ophthalmology 129.2 (2011): 152-157). GDIs were developed to treat patients with secondary glaucoma, pediatric glaucoma, and refractory glaucoma after failed trabeculectomy. Glaucoma surgical devices were introduced as a space holder to maintain the patency of the new opening, and have become recognized as one of the most important components in surgical glaucoma management. Unfortunately, the long-term outcome of GDIs has not been satisfactory, largely due to fibrotic encapsulation of the implant that impedes the drainage of fluid (Thieme H et al., Journal of glaucoma 20.4 (2011): 246-251; Anderson J M et al., Seminars in immunology. Vol. 20. No. 2. Academic Press, 2008). MIGS is a relatively new approach with a superior safety profile, but mainly targets mild to moderate glaucoma with the goal of reducing the use of glaucoma drops.

Depending on the choice of surgical devices, one-third to one-half fail within 5 years in adults, and even more rapidly in children. Failure, for all three types of glaucoma surgeries, results from the natural healing process of the human body that attempts to repair and close the new openings either at episcleral tissue for trabeculectomy (Yamanaka O et al., BMC ophthalmology 15.1 (2015): 157; Van de Velde S et al., Progress in brain research 221 (2015): 319-340) or around the implants for GDIs (Danesh-Meyer H V et al., Archives of Ophthalmology 120.6 (2002): 846-847; Gedde S J et al., American journal of ophthalmology 153.5 (2012): 789-803; Budenz D L et al., Ophthalmology 122.2 (2015): 308-316) or MIGS (Brandão L M et al., Journal of ophthalmology 2013 (2013)). It is currently thought that the foreign body reaction induced by the device causes fibrosis and scar tissue formation, leading to a dense, hypocellular, and collagen-rich capsule around the device. This builds resistance to fluid outflow and results in inadequate IOP control.

There is a need for an improved devices for controlling intraocular pressure that minimize scar tissue formation. The present invention meets this need.

SUMMARY OF THE INVENTION

In one aspect, the present invention relates to an implant device for reducing intraocular pressure, comprising: a plurality of longitudinal microchannels each having a tubular structure with a lumen running throughout; a plurality of lateral microchannels each having a tubular structure with a lumen running throughout; and a plurality of fluid outlets positioned on at least a portion of the longitudinal microchannels and lateral microchannels; wherein the plurality of lateral microchannels at least partially intersect and are in fluid connection with the plurality of longitudinal microchannels to form a flexible grid-like mesh.

In one embodiment, the longitudinal microchannels and the lateral microchannels have diameters between about 1 and 100 µm. In one embodiment, the plurality of longitudinal microchannels are spaced between about 10 and 1000 µm apart and the plurality of lateral microchannels are spaced between about 10 and 1000 µm apart. In one embodiment, the longitudinal microchannels and the lateral microchannels have diameters between about 10 and 20 µm, the plurality of longitudinal microchannels are spaced between about 100 and 200 µm apart, and the plurality of lateral microchannels are spaced between about 100 and 200 µm apart. In one embodiment, the longitudinal microchannels and the lateral microchannels have wall thicknesses between about 10 and 1000 nm. In one embodiment, the grid-like mesh has a substantially planar size of between about 50 and 500 mm$^2$.

In one embodiment, two or more grid-like meshes are stacked on top of each other and fluidly interconnected by a plurality of vertical microchannels to form a 3D mesh, each vertical microchannel having a tubular structure with a lumen running throughout. In one embodiment, the 3D mesh comprises longitudinal microchannels, lateral microchannels, and vertical microchannels having substantially similar dimensions and spacing. In one embodiment, the 3D mesh comprises longitudinal microchannels, lateral microchannels, and vertical microchannels having variable dimensions and spacing. In one embodiment, the 3D mesh comprises an inner region surrounded by an outer region, wherein the inner region comprises fluidly interconnected microchannels with diameters between about 40 and 60 µm, and the outer region comprises fluidly interconnected microchannels with diameters between about 10 µm and 20 µm.

In one embodiment, the grid-like mesh further comprises an interface fluidly connectable to a drainage tube. In one embodiment, the drainage tube comprises a pressure-sensitive valve selected from the group consisting of: a duckbill valve, a joker valve, a flapper valve, a reed valve, and a leaf valve. In one embodiment, the pressure-sensitive valve is configured to permit drainage of fluid above an intraocular pressure of between about 8 and 10 mmHg.

In one embodiment, at least a portion of the fluid outlets are positioned on short lengths of microchannel tubes fluidly connected to the longitudinal microchannels, the lateral microchannels, or both. In one embodiment, the longitudinal microchannels and the lateral microchannels are at least partially porous and permeable to fluids and molecules. In one embodiment, the plurality of longitudinal microchannels are substantially orthogonal to the plurality of lateral microchannels. In one embodiment, the longitudinal microchannels and the lateral microchannels are constructed from a material selected from the group consisting of: SU-8 photoresist, parylene, polyimide, polytetrafluoroethylene (PTFE), silicon oxides, silicon nitride, silicon carbide, and aluminum oxides.

In another aspect, the present invention relates to a method of managing intraocular pressure, comprising the steps of: providing the implant device of the present invention connected to a drainage tube; breaching the conjunctiva of an eye to access the sclera; placing the implant device against the sclera of the eye without sutures; forming a hole in the limbus of the eye adjacent to the implant device, the hole having access to the anterior or posterior chamber of the eye; threading the drainage tube through the hole; and closing the conjunctiva.

In another aspect, the present invention relates to a method of managing intraocular pressure, comprising the steps of: providing the implant device of the present invention; rolling the implant device into an elongate tubular shape; loading the implant device into a hollow syringe tip; piercing the conjunctiva of the eye with the syringe tip; and injecting the implant device into the eye such that the implant device bridges the subconjunctival space and the anterior or posterior chamber of the eye. In one embodiment, the implant device is implanted in fluid connection with a drainage tube positioned in the anterior or posterior chamber of the eye, the drainage tube having a pressure-sensitive valve.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

(FIG. 1A) An exemplary GDI device suspended in water. (FIG. 1B) Micrograph of an exemplary GDI device meshwork on substrate. The dashed box indicates the mesh area. Scale bar: 1 mm. (FIG. 1C) Magnified view of the mesh grids. Scale bar: 100 μm.

FIG. 3A depicts a schematic of a 2D mesh implant. FIG. 3B depicts a schematic of a 3D mesh implant. FIG. 3C depicts a schematic of a hybrid 3D mesh implant. FIG. 3D depicts a newly fabricated 3D mesh implant. FIG. 3E depicts a magnified view of a 3D mesh implant.

(FIG. 4A) The flexibility of the MIGS stent device allows for the MIGS stent device to be loaded into a syringe tip. (FIG. 4B) The MIGS stent device bridges the subconjunctival space and the anterior or posterior chamber for fluid drainage and intraocular pressure management.

(FIG. 9A) The AGV implant. (FIG. 9B) The microfluidic meshwork. Inset figures are magnified views of the microfluidic meshwork.

(FIG. 10A) Capsule beneath the plate of AGV. (FIG. 10B) Minimal reaction to the meshwork in rabbit 1, inset figure is a magnified view to a single channel of the meshwork (400×). (FIG. 10C) Minimal reaction to the meshwork in rabbit 2. (FIG. 10D) Minimal reaction to the meshwork in rabbit 3. Arrows in FIG. 10B through FIG. 10C are to delineate the meshwork.

DETAILED DESCRIPTION

Figure 1:
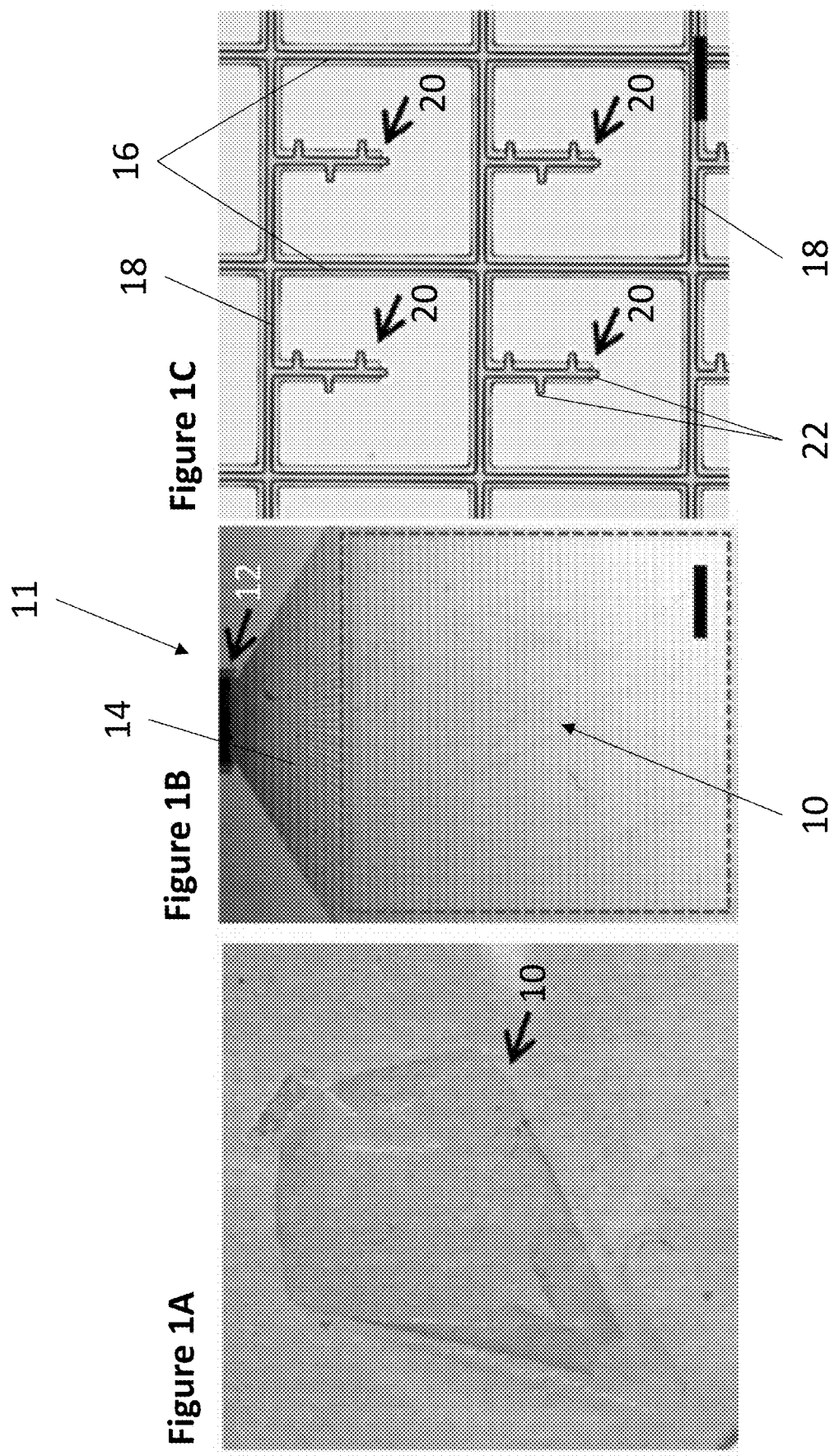
FIG. 1A through FIG. 1C depicts various magnified views of an exemplary mesh and glaucoma drainage implant (GDI) device.

The present invention provides for novel glaucoma surgical devices comprising a microfluidic meshwork. The meshwork comprises interconnected, cellular-dimensioned microfluidic channels. Excess fluid in the eye can be drained and diffused through the microfluidic channels. The meshwork is porous and highly flexible, affording mechanical compliance similar to that of eye tissue. The meshwork minimizes foreign body reactions to the implant, decreasing fibrosis and capsule formation.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween about. This applies regardless of the breadth of the range.

Glaucoma Drainage Meshwork

In one aspect, the present invention provides improved mesh implants for glaucoma drainage. The improved implants feature a microfluidic meshwork having high flexibility, high porosity, and mechanical compliance similar to eye tissue that reduces fibrosis and capsule formation.

Referring now to FIG. 1A, the outlined region of FIG. 1B, and FIG. 1C, an exemplary glaucoma implant mesh 10 is depicted. Mesh 10 comprises a plurality of longitudinal microchannels 16 fluidly connected to a plurality of lateral microchannels 18. Longitudinal microchannels 16 and lateral microchannels 18 can be connected orthogonally or at any suitable angle.

Figure 2:
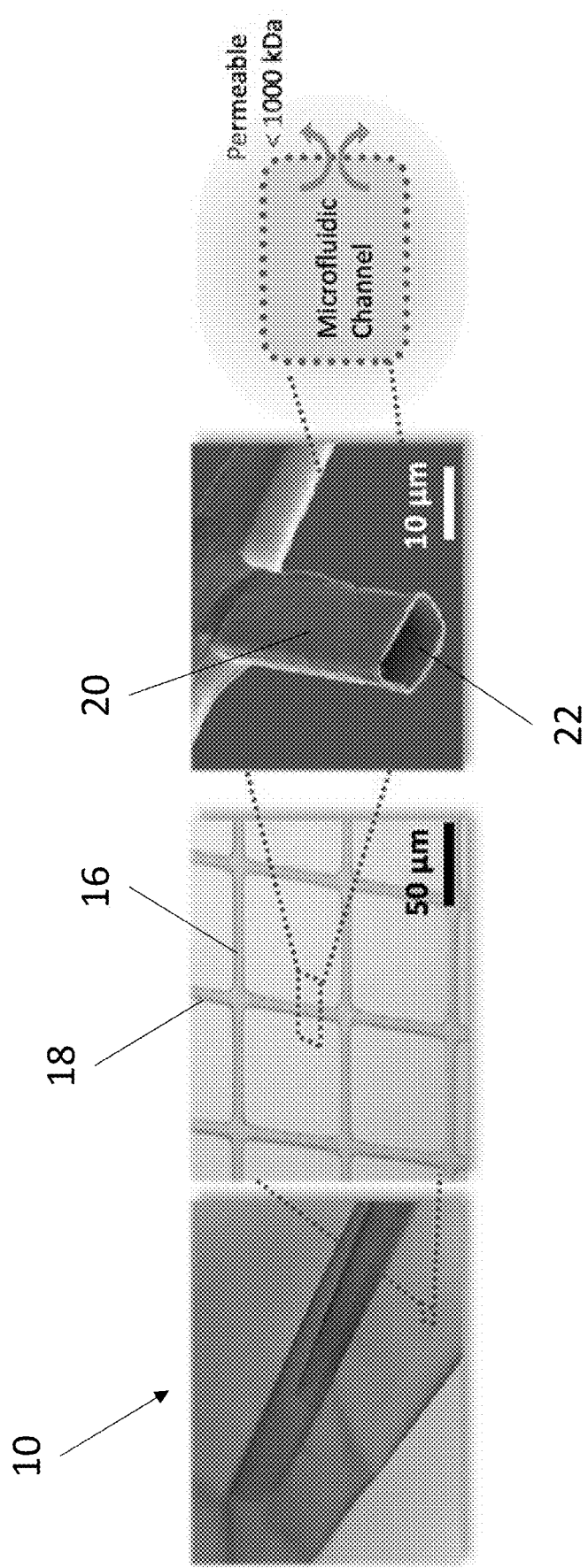
FIG. 2 depicts various magnified views of an exemplary mesh implant for glaucoma drainage.

Referring now to FIG. 2, longitudinal microchannels 16 and lateral microchannels 18 are elongate tubular structures having a lumen running throughout. Longitudinal microchannels 16 and lateral microchannels 18 can have any suitable geometry. For example, longitudinal microchannels 16 and lateral microchannels 18 can have circular cross sections, ovoid cross sections, polygonal cross sections, or combinations thereof. Longitudinal microchannels 16 and lateral microchannels 18 can have a wall thickness of between 10 and 1000 nm. Longitudinal microchannels 16 and lateral microchannels 18 can have any suitable diameter, such as a diameter between about 1 and 100 µm or more. For example, the diameter can be between about 10 and 20 µm to form narrow diameter microchannels, and the diameter can be between about 40 and 60 µm to form wide diameter microchannels. Microchannels having a diameter between about 10 and 20 µm have superb tissue compatibility with minimal fibrosis. In some embodiments, one or more longitudinal microchannels 16, lateral microchannels 18, or both are porous along at least one section of their length. Porous sections of the microchannels can be permeable to fluids as well as molecules, such as molecules having molecular weights up to 1 MDa or more. The physical characteristics of longitudinal microchannels 16 and lateral microchannels 18 provide mesh 10 with high flexibility and compliance, permitting mesh 10 to conform to natural tissue movements with minimal inflammation, irritation, and scar tissue formation. In certain embodiments, longitudinal microchannels 16 and lateral microchannels 18 can have variable thicknesses such that the flexibility of one or more sections of mesh 10 can be tuned.

In certain embodiments, mesh 10 can have a lattice structure with at least one branch 20 having at least one outlet 22 in each open space of the lattice. As shown in FIG. 1C and FIG. 2, exemplary branches 20 are tubular structures having a lumen running throughout that are fluidly connected to and extend from lateral microchannels 18, longitudinal microchannels 16, or any combination thereof. In some embodiments, branches 20 can have the same or different porosity from longitudinal microchannels 16 and lateral microchannels 18. Fluid outlets 22 are apertures that open into the lumen of branches 20. In certain embodiments, fluid outlets 22 may also be positioned directly on longitudinal microchannels 16, lateral microchannels 18, or both.

The drainage rate and drainage characteristics of mesh 10 can be adjusted in many aspects. For example, the drainage rate can be increased or decreased by tuning the porosity of the microchannels and by increasing or decreasing the number of branches 20 and fluid outlets 22. The drainage characteristics can be modified by varying the porosity and the placement of branches 20 and fluid outlets 22 in different regions of mesh 10. In another example, increasing the density of microchannels may increase the drainage rate of mesh 10. The density of microchannels can be described as the "period," or distance between about parallel microchannels. For example, each longitudinal microchannel 16 can be spaced apart by a distance between about 10 and 1000 µm, and each lateral microchannel 18 can be spaced apart by a distance between about 10 and 1000 µm. In one embodiment, a spacing of between about 100 and 200 µm provides superb tissue compatibility with minimal fibrosis. In some embodiments, the period of mesh 10 is uniform throughout. In certain embodiments, sections of mesh 10 can have different periods. In other embodiments, sections of mesh 10 can have varying periods, in patterns such as a gradient that increases or decreases in periodicity.

Figure 3C:
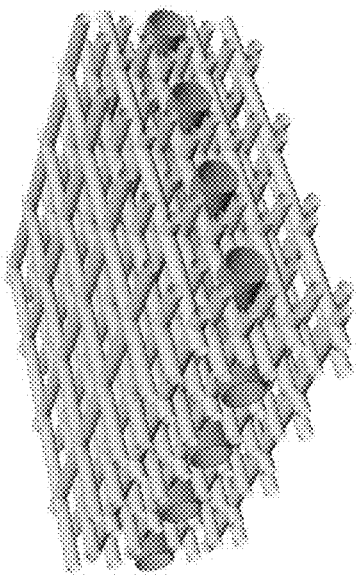
FIG. 3A through FIG. 3E depict additional images of exemplary mesh implants.
Figure 3B:
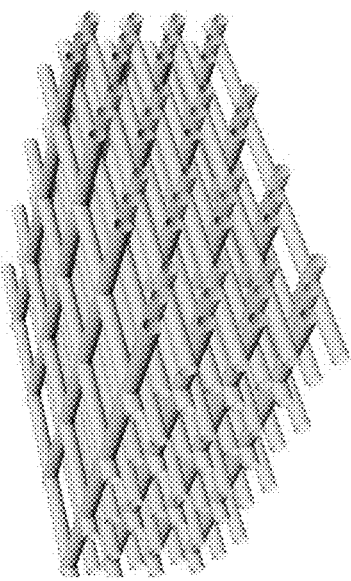
Figure 3A:
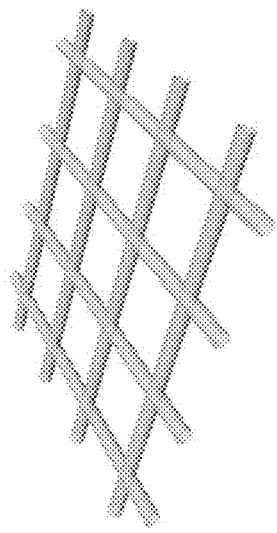
Figure 3E:
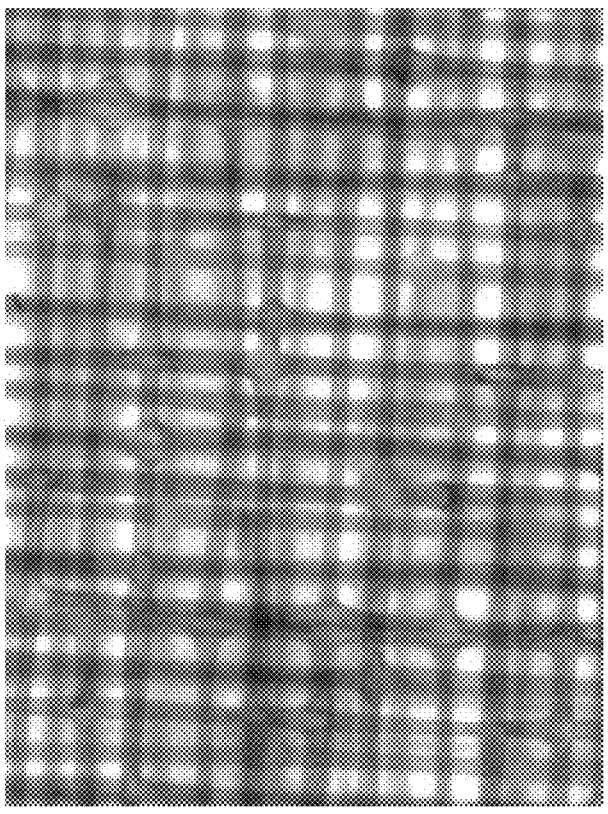
Figure 3D:
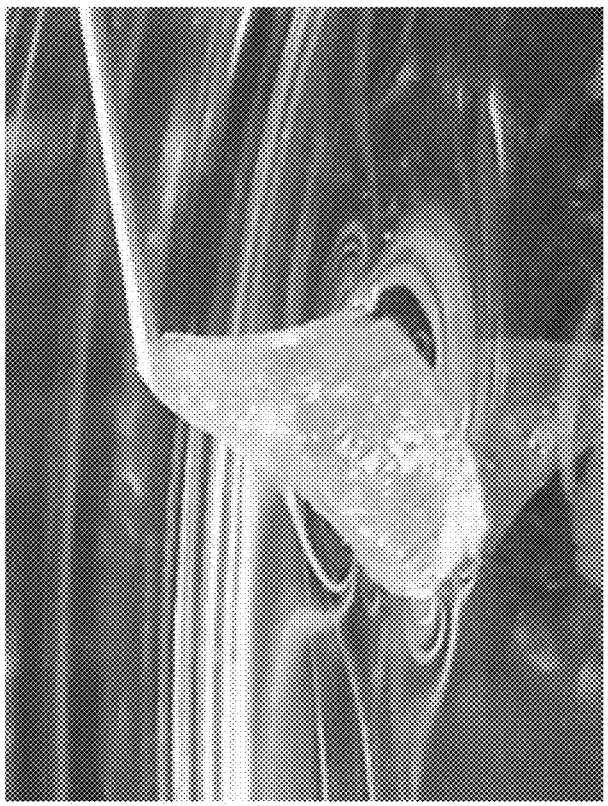

Referring now to FIG. 3A through FIG. 3E, several exemplary constructions of mesh 10 are shown. FIG. 3A depicts a 2D mesh 10 as described elsewhere herein. A 2D mesh 10 has a substantially planar shape and may advantageously fit between about tissue layers with minimal discomfort. Mesh 10 can be dimensioned to match the surface areas of existing glaucoma drainage devices, in the range of between about 50 and 500 mm$^2$. In FIG. 3B, a 3D mesh is depicted. A 3D mesh can be constructed from 2, 3, 4, 5, 10, 15, 20, 30, 50, or more mesh 10 stacked together. A 3D mesh can also be fabricated into a single interconnected structure having intersecting longitudinal microchannels 16 and lateral microchannels 18 forming layers of mesh 10, as well as vertical microchannels fluidly interconnecting each mesh 10 layer. In FIG. 3C, a 3D hybrid mesh is depicted. A 3D hybrid mesh can be constructed from a stack of one or more mesh 10 having varying diameters, periods, and number and arrangements of branches 20 and fluid outlets 22. The 3D hybrid mesh can also be fabricated into a single interconnected structure having intersecting longitudinal microchannels 16 and lateral microchannels 18 with varying diameters, periods, and number and arrangements of branches 20 and fluid outlets 22 to form different layers of mesh 10, as well as vertical microchannels with varying diameters, periods, and number and arrangements of branches 20 and fluid outlets 22 that fluidly interconnect each mesh 10 layer. In some embodiments, the 3D hybrid mesh can include an inner region having wide diameter microchannels surrounded by an outer region having narrow diameter microchannels. As described elsewhere herein, microchannels having a diameter between about 10 and 20 μm and a spacing of between about 100 and 200 μm between about each microchannel provides superb tissue compatibility with minimal fibrosis. In this configuration, the inner region having wide diameter microchannels can provide at least 10 fold or more flow conduction while being insulated from eliciting tissue reactions by the outer region having narrow diameter microchannels.

Glaucoma Drainage Implant Device

In some embodiments, mesh 10 can be integrated with fluid funneling features to form a glaucoma drainage implant (GDI) device. In general GDI devices comprise a tube connected to a plastic plate. The plastic plate is sewn onto the surface of the sclera of an eye, a hole is made into the eye at the limbus, and the tube is inserted through the hole into the anterior or posterior chamber of eye, whereby intraocular fluid is able to drain through the tube and out of the plate. After implantation, the plate is susceptible to developing fibrosis and scar tissue, and is only able to afford limited protection against blocking the opening of the tube. As described elsewhere herein, the meshwork of the present invention enables drainage while minimizing foreign body reactions to the implant, enhancing the performance of a GDI device replacing the plate with the meshwork to decrease fibrosis and capsule formation.

Figure 7:
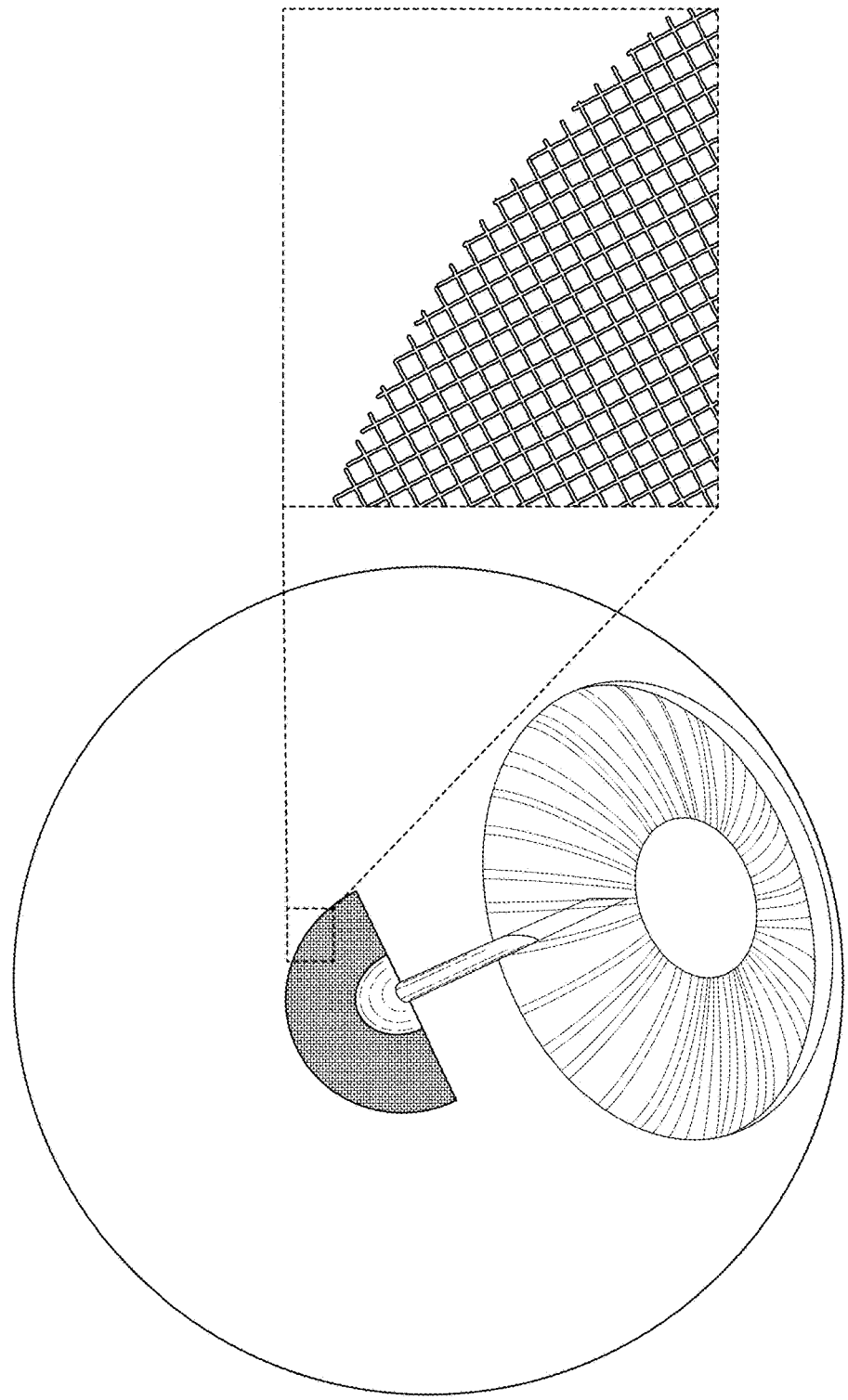
FIG. 7 depicts a conceptual GDI device. The plate of a traditional GDI is replaced by the microfluidic meshwork.

With reference to FIG. 1B, an exemplary GDI device 11 comprises interface 12 fluidly connected to distributing section 14, which is in turn fluidly connected to mesh 10. Interface 12 can be adapted to fluidly connect to one or more suitable glaucoma drainage tubes commonly used in the art (FIG. 7). Glaucoma drainage tubes are generally constructed from a flexible, biocompatible material. In some embodiments, glaucoma drainage tubes can include a pressure-regulating mechanism to prevent excess draining of fluid. For example, a glaucoma drainage tube can include a pressure-sensitive valve positioned within the lumen of the tube. The pressure-sensitive valve may be tuned to open at high intraocular pressures to drain excess fluid from the anterior or posterior chamber of the eye. As fluid is drained from the anterior or posterior chamber, intraocular pressure decreases to the point where there is insufficient pressure to keep the pressure-sensitive valve open, whereupon the valve closes and prevents further draining of fluid. In various embodiments, the pressure-sensitive valve can be a one-way valve to prevent backflow of drained fluid. The pressure-sensitive valve can be any suitable valve, including but not limited to a duckbill valve, a joker valve, a flapper valve, a reed valve, a leaf valve, and the like.

Distributing section 14 directs fluid from the one or more glaucoma drainage tubes to mesh 10. In some embodiments distributing section 14 can be porous, partially porous, or nonporous. A nonporous distributing section 14 ensures that fluid is transported to mesh 10 before being released into the surrounding tissue, preventing the buildup of fluid immediately adjacent to interface 12. Mesh 10 has a thin construction and a tissue-like mechanical compliance, enabling its attachment to an eye with minimal discomfort and scarring while maintaining fluid conductance.

MIGS Stent Device

In some embodiments, mesh 10 can be constructed to form a minimally invasive glaucoma surgery (MIGS) stent device. MIGS implants provide intraocular pressure lowering surgical interventions while minimizing complications associated with other procedures, such as filtration surgery. MIGS devices are generally tube-like units that drain intraocular aqueous fluid into a variety of anatomical compartments in the eye to relieve intraocular pressure. As these devices shunt fluid between about compartments, they are susceptible to failure due to scarring from fibroblast invasion. As described elsewhere herein, the meshwork of the present invention enables drainage while minimizing foreign body reactions to the implant, enhancing the performance of a MIGS device incorporating the meshwork to decrease fibrosis and capsule formation.

Figure 4B:
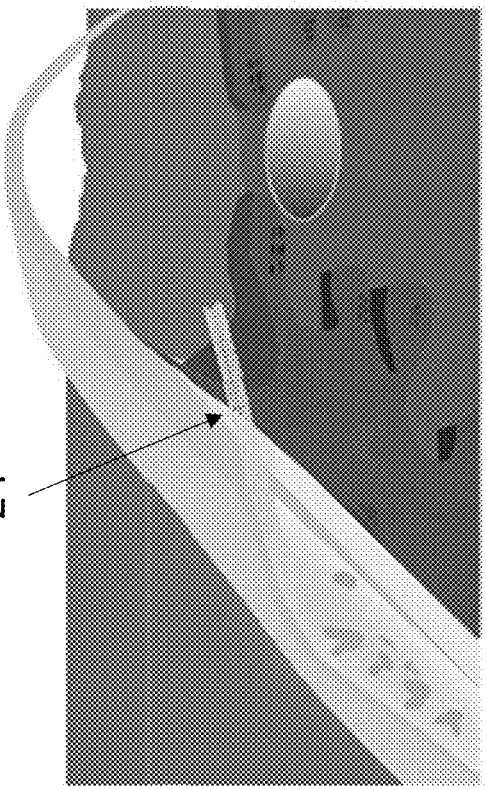
FIG. 4A and FIG. 4B depicts illustrations of an exemplary method of implanting a MIGS stent device.
Figure 4A:
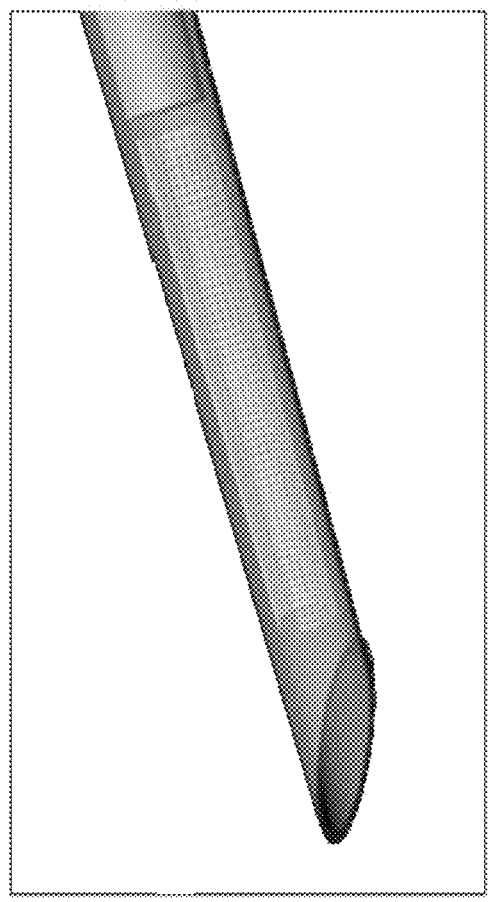

With reference to FIG. 4A and FIG. 4B, an exemplary MIGS stent device 24 is depicted. Device 24 comprises mesh 10 in an elongate tube configuration having a length that can span the distance between about a site having excess fluid and a site capable of accepting excess fluid. In some embodiments, device 24 is connectable to a glaucoma drainage tube, as described elsewhere herein. A glaucoma drainage tube can increase the distance between about a site in need of fluid drainage and a site capable of accepting excess fluids. A glaucoma drainage tube can also provide pressure-regulating mechanism to prevent excess draining of fluid.

It should be understood that device 24 is not limited to a tube configuration, and is amenable to any shape and size suitable for draining intraocular aqueous fluid. For example, device 24 can comprise a length of 2D mesh 10, 3D mesh 10, or 3D hybrid mesh 10 in an unfolded planar configuration or folded into an elongate circular shape, ovoid shape, triangular shape, rectangular shape, polygonal shape, and the like. In another example, device 24 can comprise a length of 3D mesh 10 or 3D hybrid mesh 10 in an elongate cylindrical shape, elliptic cylindrical shape, prismic shape, polyhedron shape, and the like. In certain embodiments, device 24 can include one or more branches, such that intraocular aqueous fluid can be drained from one or more branches and be deposited into two or more sites capable of accepting excess fluids by the one or more branches. Device 24 is foldable and compressible to fit within the lumen of a hollow syringe tip. The ability of device 24 to be loadable into a hollow syringe tip enhances minimally invasive delivery of device 24 by injection into an eye through a single needle puncture.

Methods of Making

Figure 5:
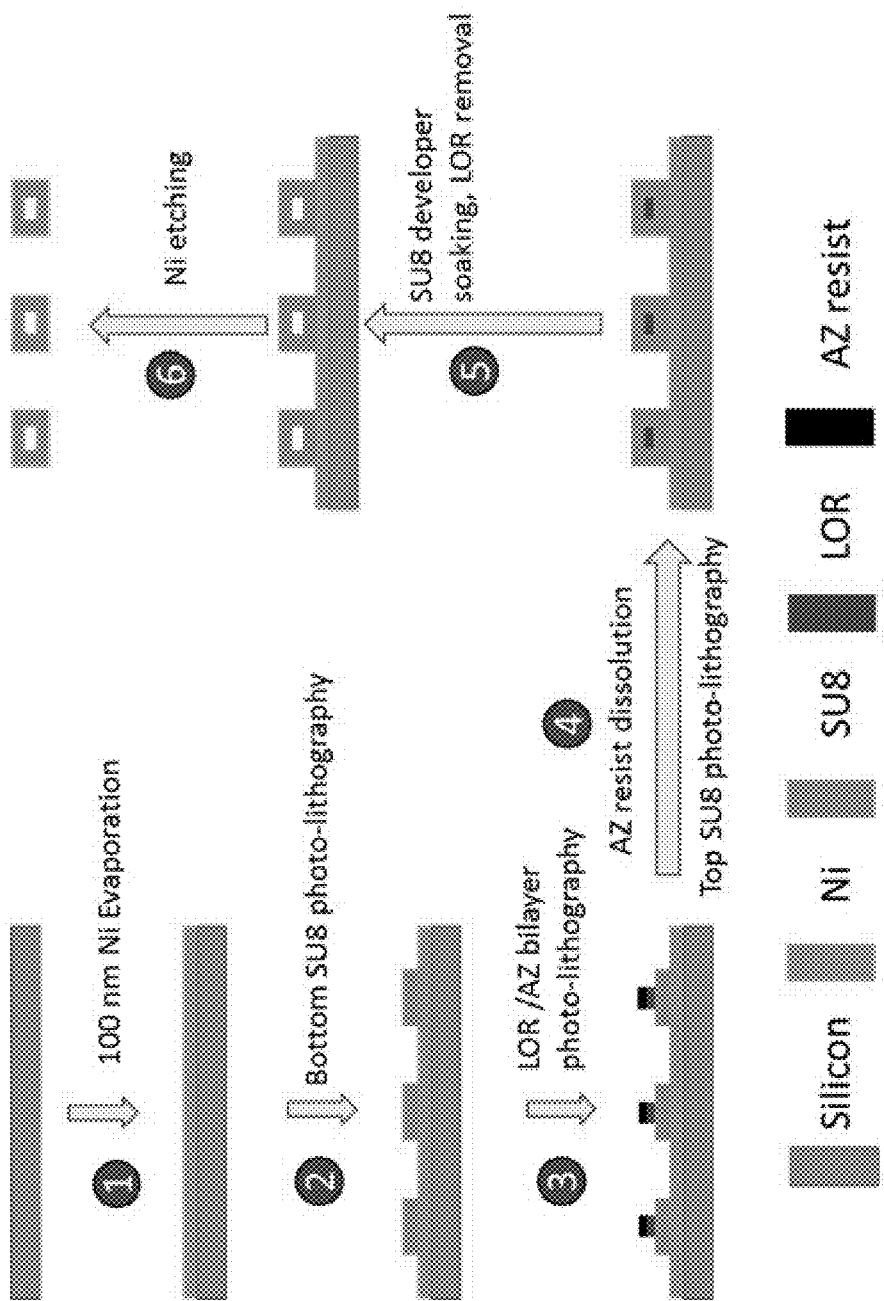
FIG. 5 depicts a diagram of an exemplary method of fabricating a mesh implant for glaucoma drainage.

In another aspect, the present invention provides methods for making the glaucoma drainage meshes. In one embodiment, the method of making a mesh comprises photolithography. An exemplary diagram is shown in FIG. 5. In step 1, a releasing layer is coated on a substrate, such as a silicon wafer, by thermal evaporation. The releasing layer can be any suitable material, such as nickel, and can have any suitable thickness, such as in the range of 10 to 1000 nm. In step 2, a layer of mesh material is deposited on the releasing layer to define the bottom surface of the mesh microchannels. Non-limiting examples of mesh materials include polymers such as SU-8 photoresist, parylene, polyimide, and polytetrafluoroethylene (PTFE), and inorganic materials such as silicon oxides, silicon nitride, aluminum oxides, silicon carbide, and the like. In step 3, one or more sacrificial layers are deposited on the mesh material. The sacrificial layers can be formed from any suitable dissolvable material, such as LOR 5A photoresist, AZ1505 photoresist, AZ159 photoresist, polymethyl methacrylate (PMMA) fibers, glass fibers, nickel foam, copper foam, gold foam, gelatin foam, and the like. In step 4, additional mesh material is deposited to define the upper surfaces of the mesh microchannels, wherein one or more sacrificial layers are dissolved in the process. In step 5, the remaining sacrificial layer is dissolved. In step 6, the mesh microchannels are released from the substrate by etching away the releasing layer. The mesh microchannels can then be processed as appropriate, such as by wash and sterilization steps. The mesh microchannels can be stored in a buffer solution for preservation prior to implanting.

Figure 6:
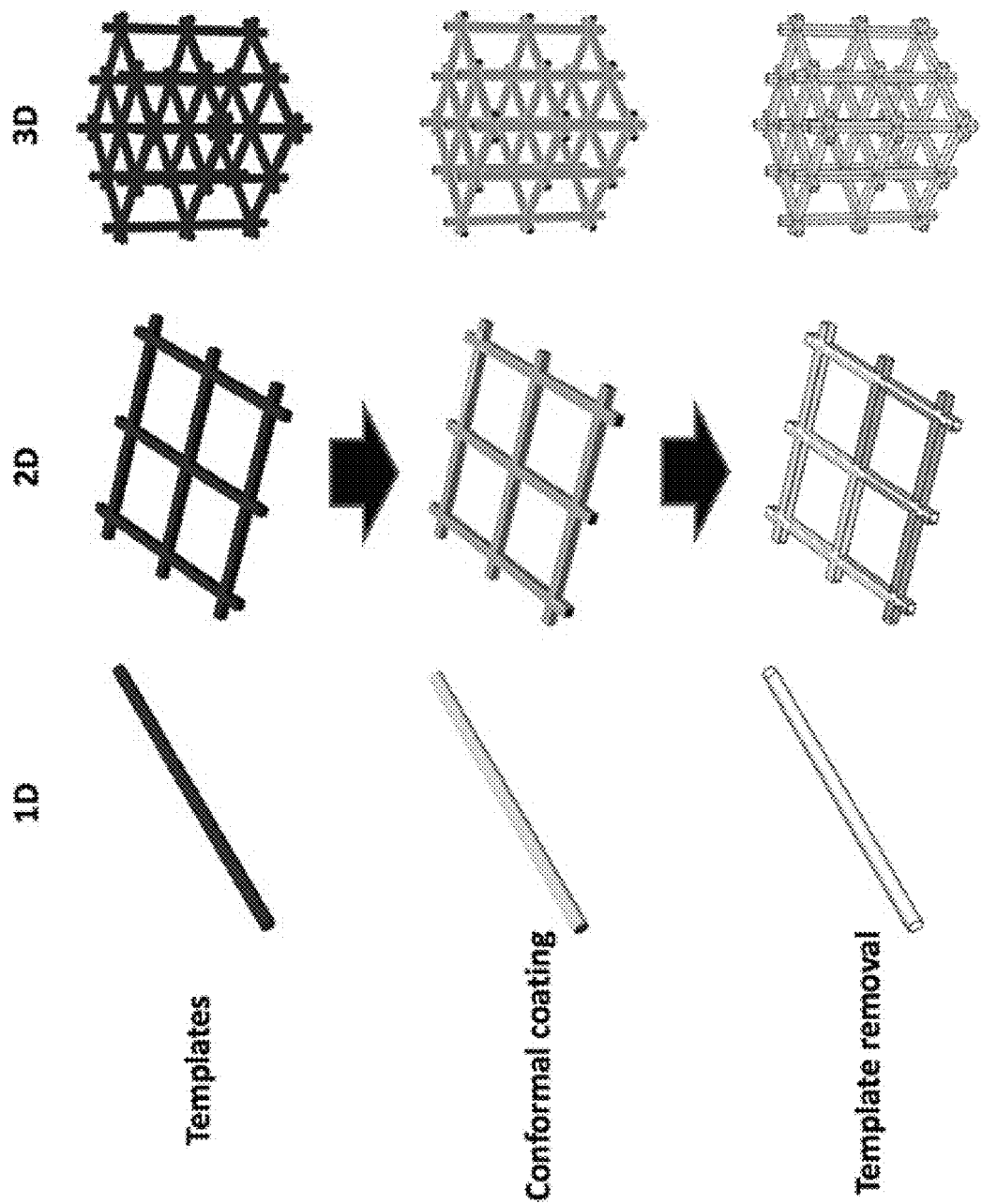
FIG. 6 depicts a diagram of another exemplary method of fabricating a mesh implant for glaucoma drainage.

In another embodiment, the method of making a mesh comprises drawing and coating a sacrificial template. Referring now to FIG. 6, a diagram showing general steps of making one, two, and three dimensional glaucoma drainage meshes is depicted. The sacrificial template can be formed from any suitable dissolvable material, such as LOR 5A photoresist, AZ1505 photoresist, AZ159 photoresist, PMMA fibers, glass fibers, nickel foam, copper foam, gold foam, gelatin foam, and the like. The sacrificial templates can be formed on a substrate with a releasing layer. After forming a sacrificial template, the sacrificial template is coated with a preferably biocompatible material to form the mesh microchannels. The coating can have a thickness of between about 10 and 1000 nm. The thickness of the coating can be adjusted to control the porosity/permeability of the mesh microchannels. Non-limiting examples of coatings include polymers such as SU-8 photoresist, parylene, polyimide, and polytetrafluoroethylene (PTFE), and inorganic materials such as silicon oxides, silicon nitride, aluminum oxides, silicon carbide, and the like, and the coatings can be applied using appropriate methods such as vapor phase polymer coating, liquid phase polymer coating, atomic layer deposition, spin coating, dip coating, chemical solution deposition, liquid bath immersion, and the like. The mesh microchannels are completed after dissolving the sacrificial template and etching away the releasing layer.

In some embodiments, the mesh can be subject to one or more surface treatments. The surface treatments can enhance the compatibility of the mesh implant and provide one or more treatments to the site of implant. In various embodiments, the surface treatments can include a therapeutic comprising a natural or a synthetic drug, including but not limited to: analgesics, anesthetics, antifungals, antibiotics, anti-inflammatories, nonsteroidal anti-inflammatory drugs (NSAIDs), anthelmintics, antidotes, antihistamines, anticancer drugs, antimicrobials, antivirals, chemotherapeutic agents, corticoids (such as steroids), radiation sensitizers, calcineurin inhibitors, antiproliferative agents, mTOR inhibitors, and the like.

In some embodiments, the biocompatibilty of the mesh can be improved (i.e., modified) with chemicals such that the subsequent healing response of surrounding tissue is enhanced after implantation. The alteration in healing response can include a reduction in inflammatory response typically seen with polymeric materials, such as a reduced presence of macrophages and foreign body giant cells. The chemical modifications may include the covalent interaction of the chemical species with polymer. In addition, the chemical modifications may include the absorption of the applied chemical species into the polymers. These chemical modifications include the use of proteins and peptides with known effects on cellular function, such as the reduction in inflammation, reduction in fibrous capsule formation by inhibiting the proliferation of cells found in developing fibrous capsules, and/or the inhibition of extracellular matrix protein synthesis by cells in developing fibrous capsules. The chemical treatment may include any one, or a combination of, extracellular matrix proteins selected from the group consisting of collagen type I, collagen type III, collagen type IV, osteopontin, laminin type 1, laminin type 5, laminin type 10/11, fibronenctin, and peptide sequence RGD.

Methods of Use

In another aspect, the present invention provides methods for using the mesh implants for glaucoma drainage. As described elsewhere herein, the mesh implants of the present invention are useful in draining excess fluid in the eye to relieve intraocular pressure while minimizing scar tissue formation. The mesh implants are amenable to surgical insertion methods used in the art for existing drainage implants.

In some embodiments, the present invention provides methods of implanting GDI devices. The GDI devices of the present invention are compatible with drainage tubes commonly used in the art. Accordingly, typical implant procedures for glaucoma draining devices can be adapted for implanting the GDI devices of the present invention. For example, the GDI devices of the present invention can be placed on the subconjunctiva after conjunctival peritomy, with the drainage tube positioned in the subconjunctival area and the anterior or posterior chamber to receive excess fluid. A typical procedure involves making an incision in the conjunctiva to expose the sclera. The mesh portion of a GDI device can then be placed against the sclera. Advantageously, the GDI devices can be placed without the need for sutures. A full thickness hole can be made in the limbus of the eye, such as with a needle having a gauge substantially similar to the gauge of the drainage tube. The drainage tube can then be inserted through the hole to extend into the anterior or posterior chamber of the eye, whereupon intraocular fluid can be drained from the anterior or posterior chamber through the drainage tube and distributed out of the mesh portion.

In some embodiments, the present invention provides methods of implanting MIGS devices. Referring now to FIG. 4A and FIG. 4B, an exemplary method for implanting a MIGS stent device is depicted. The high flexibility of the mesh implant enables the MIGS stent device to be folded or compressed to a size that is loadable into a hollow syringe tip. The syringe tip can then be used to introduce the MIGS stent device into the eye to bridge the anterior or posterior chamber with an adjacent site of the eye to receive drained fluid. The adjacent site of the eye can be any suitable anatomy commonly used to divert intraocular fluid, including Schlemm's canal, the sclera, and the uveosceral routes.

After injecting the MIGS stent device, the syringe tip can be extracted to leave the MIGS stent device in place. The delivery method avoids incisions in the conjunctiva to minimize trauma and complications. The subconjunctival area is targeted due to its broad area, and draining excess fluid to the subconjunctival area can reduce intraocular pressure to a range of 8 to 10 mmHg. In some embodiments, the MIGS stent device can be inserted 5-10 mm posterior to the limbus to avoid the formation of a cystic bleb near the limbus.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: A Novel Flexible Microfluidic Meshwork to Reduce Fibrosis in Glaucoma Surgery The following study presents the concept for a modified GDI (FIG. 7). The device design is based on that of the conventional GDI; however, the solid plate was replaced with a microfluidic meshwork in the fluid drainage region. The design of the meshwork was inspired by recently developed brain implants that can suppress chronic foreign body reactions (Xie C et al., Nature materials 14.12 (2015): 1286-1292). Two key features of the brain implants were incorporated into the microfluidic meshwork design. Firstly, it consists of interconnected, cellular-dimensioned microfluidic channels that can conduct fluid. Secondly, it is ultra-flexible and conforms to the curvature and movement of the eye tissue after implantation. It was hypothesized that these two features combined minimize fibrotic tissue formation around the meshwork, and therefore reduce the risk of failure of the drainage implants. In this work, as the initial test of the viability of this concept, the chronic tissue reactions to the implanted microfluidic meshwork alone were investigated, where no tube was connected to the meshwork in the rabbit model. The plate of the conventional GDI, Ahmed glaucoma valve (AGV, PF7 model), was used as the control.

The materials and methods are now described.

Meshwork Fabrication

The drainage devices were fabricated using photolithography techniques similar to those that were demonstrated previously (Liu J et al., Proceedings of the National Academy of Sciences 110.17 (2013): 6694-6699). The fabrication was done on silicon wafers with a nickel-releasing layer. Briefly, microchannel walls were patterned with negative photoresist SU-8 and the microchannels were formed by sacrificial photoresist (LOR 5A and AZ1505, Microchem, Westborough, MA). The meshwork had an overall area of 7 mm×7 mm and a grid period of 100 µm. The thickness of the meshwork was 4 µm. The microfluidic channels had outer diameters of 20 µm and inner diameters of 8 µm. These parameters were determined according to finite element simulations to provide sufficient AH outflow (2 µL/min at 10 mmHg). After being released from the substrate, the meshworks were washed and stored in buffer solution prior to autoclave and implantation. The design, fabrication and simulation of the meshwork is documented elsewhere in detail (Wei X, Lee J, H., Zhao Z, Amoozgar B, He F, Bloomer M, et al. Ultra-flexible Microfluidic Meshwork for Minimally Invasive Glaucoma Surgery).

Animal Preparation and Standard Surgical Implantation

Figure 8:
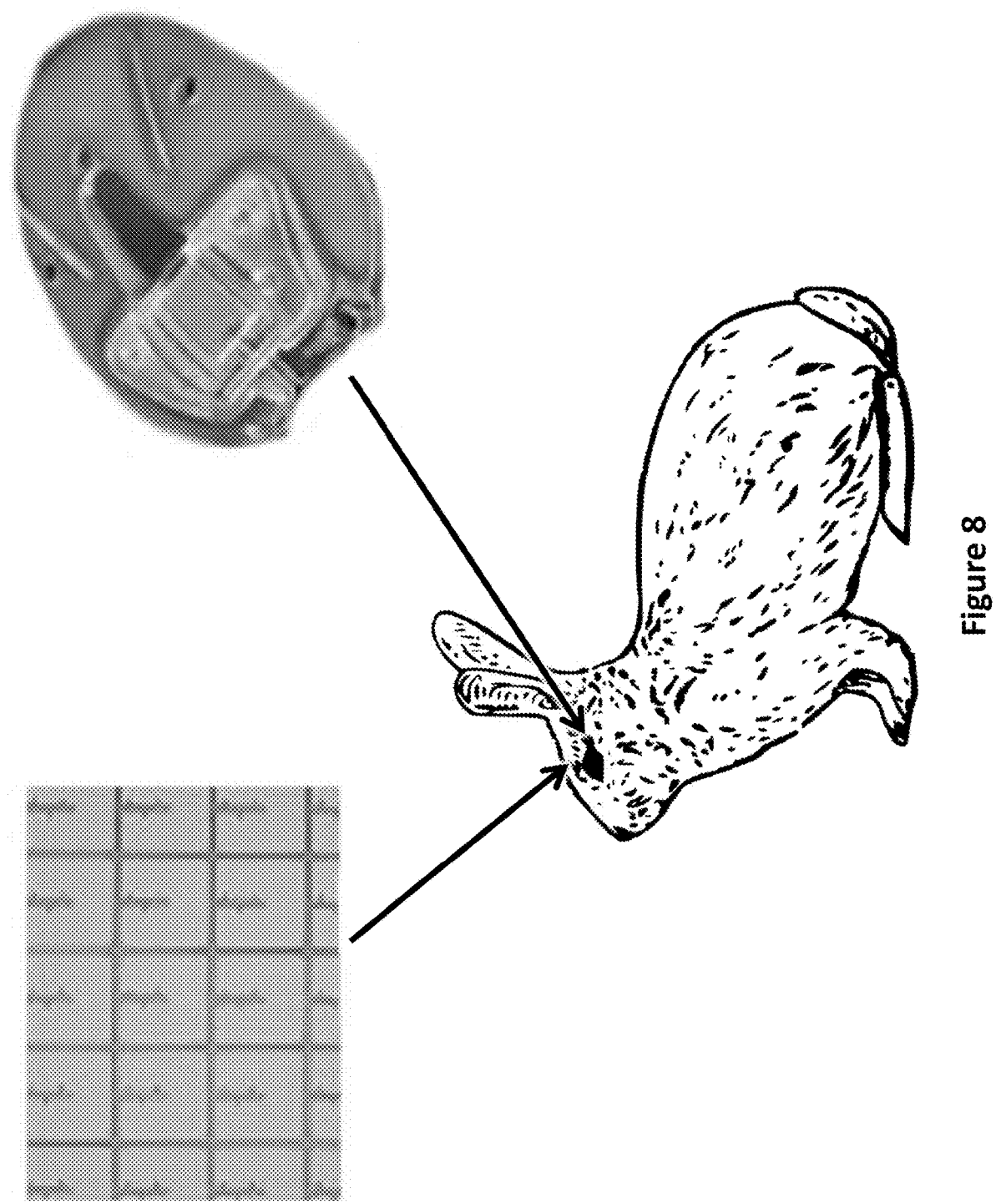
FIG. 8 depicts the implantation of the implants in rabbit eyes. One eye was assigned to the conventional AGV PF7 silicone plate and the other to the microfluidic meshwork. No tube was connected with either AGV PF7 plate or the microfluidic meshwork.

Three healthy Albino New Zealand rabbits (12-14 weeks old, and weighing 2-3 kg) were used. For each rabbit, the eyes were randomized to have one assigned to the current AGV PF7 silicone plate (no tube connected) and the other to the microfluidic meshwork (FIG. 8). Under an operating microscope, the rabbits were anesthetized using an intramuscular injection of a mixture of ketamine hydrochloride (50 mg/kg) and xylazine hydrochloride (10 mg/kg), followed by mask anesthesia of isoflurane (2-4%). All efforts were made to minimize suffering of the animals. Both eyes were then prepared with povidone-iodine. For each eye, 6-0 Vicryl suture was passed through the supratemporal limbus to rotate the eye downward. Conjunctival peritomy was performed at the limbus in the supratemporal quadrant, followed by posterior dissection in the same plane. The flexible microfluidic meshwork was placed without suture and the AGV FP7 plate was sutured with 9-0 nylon sutures onto the episcleral surface approximately 6 mm from the limbus. The conjunctiva was closed with interrupted 8-0 vicryl sutures. There was no communication with the anterior or posterior chamber with either implant. To facilitate visualization of the microfluidic meshwork, a limbal 10-0 nylon suture was placed at the middle of the microfluidic meshwork. At the end of the surgery, subconjunctival cefazolin 0.1 ml was given for antimicrobial prophylaxis. As routine postoperative care, the rabbit eyes were treated with Polymyxin antibiotic drops for one week and prednisolone acetate 1% drops starting with 3 times a day and then tapered every 3 days. All animal eyes were examined for signs of infection and plate erosion on days 1, 3, 7, and 14 and monthly thereafter for up to 3 months. Three months after surgery, the rabbits were euthanized by intravenous injection of potassium chloride or sodium pentobarbital after being anesthetized by isoflurane or ketamine/xylazine combination.

Histology Preparation

Three months after surgery, the rabbits were sacrificed and exenterations were performed in which the entire orbital contents were removed. Precautions were taken not to disturb the implants. After being fixed with 10% formalin, the eyes were dissected. Histology slides of the implant and the surrounding tissues were prepared and stained with hematoxylin-eosin (HE). The histological sections were examined and measured using light microscopy by a pathologist who was blinded to the different groups. Capsule thickness at the bottom of the plate was measured for each eye.

Statistical Considerations

Paired student's t-test was applied to compare the difference in the thickness of fibrous capsule between about the microfluidic meshwork and conventional AGV PF7 plate groups. The rate of infection/plate erosion and any other notable side effects were compared between about the two groups using the Fisher exact test.

The results are now described.

Six eyes from 3 New Zealand rabbits underwent implantation of the plate of AGV PF7 in one eye and the microfluidic meshwork in the other in a randomized fashion. Two left eyes and one right eye received AGV PF7 while the other two right eyes and one left eye received the microfluidic meshwork. There was no tube connected to either AGV PF7 or the microfluidic meshwork. No significant complications were noticed during the implantation of both AGV PF7 and the microfluidic meshwork.

Figure 9A:
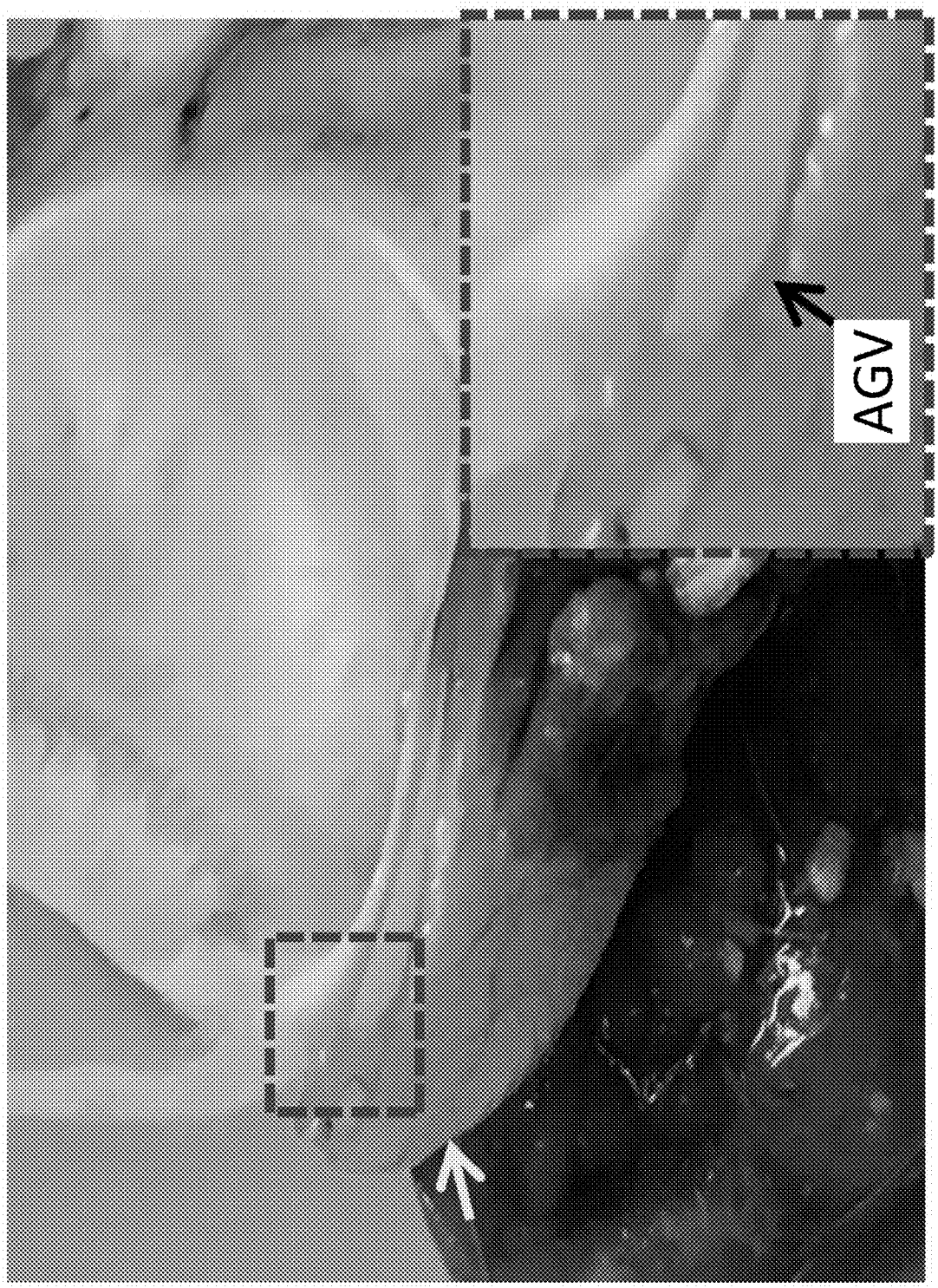
FIG. 9A and FIG. 9B depict the gross section of tissue reactions to the microfluidic meshwork in comparison with AGV 3 months post implantation.
Figure 9B:
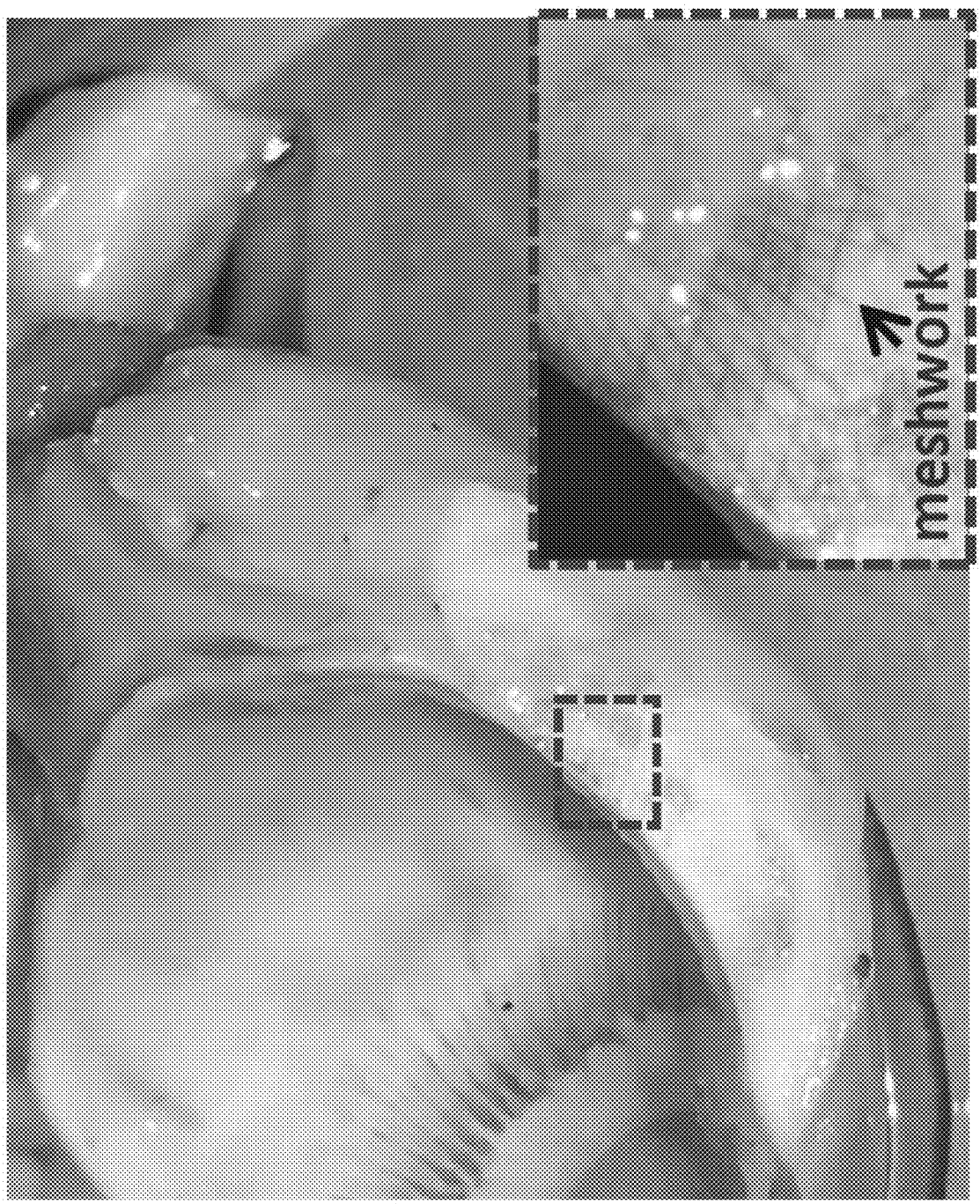
Figure 10B:
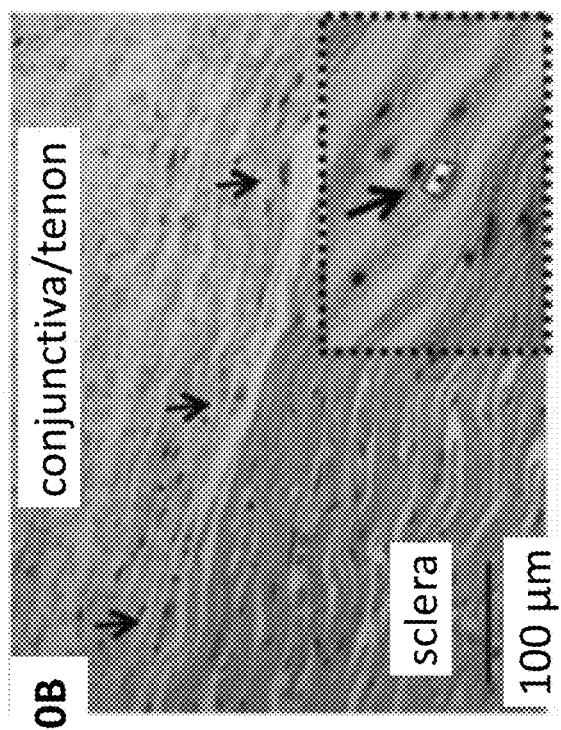
FIG. 10A through FIG. 10D depict the histological study of tissue reaction to the microfluidic meshwork in comparison with AGV 3 months post implantation.
Figure 10D:
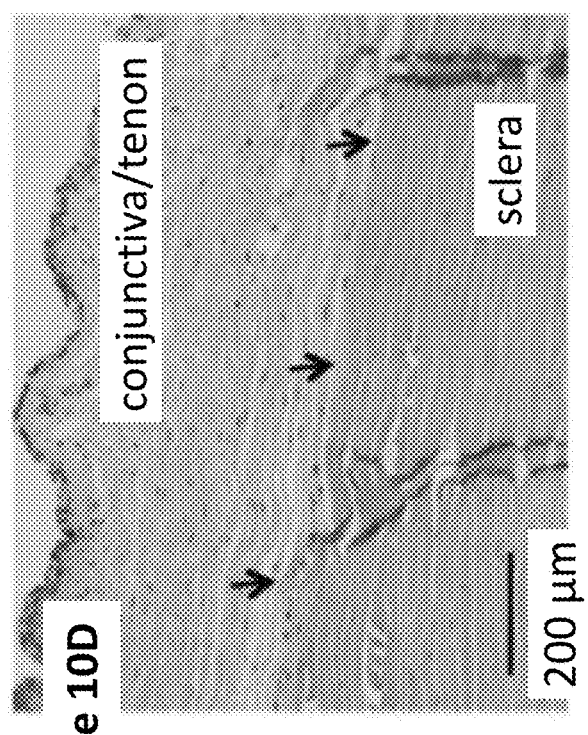
Figure 10A:
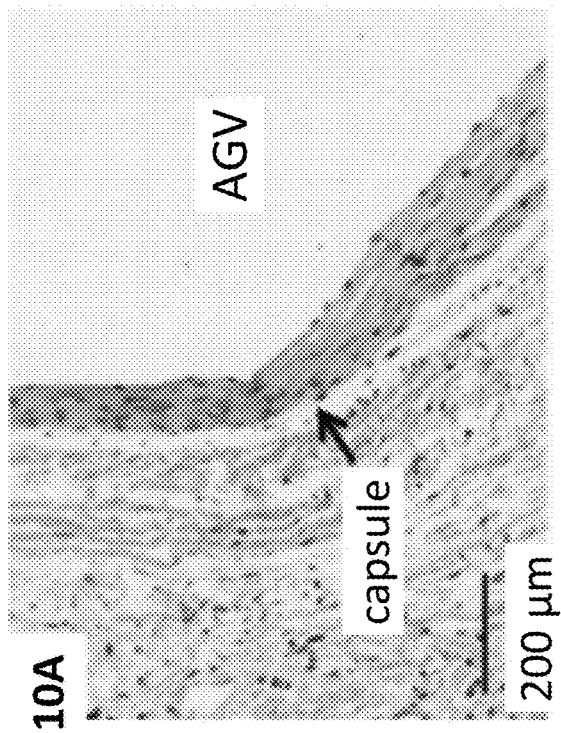
Figure 10C:
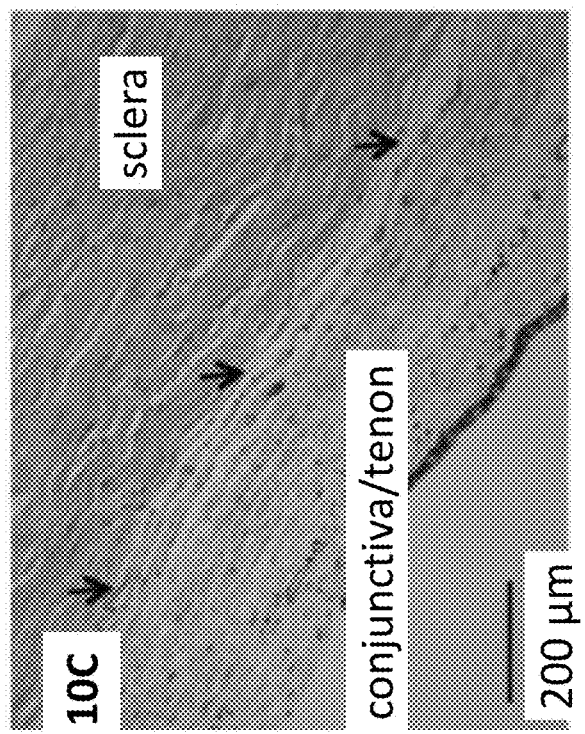

During the postoperative visits, there were no signs of infections, inflammation or erosion in any eye. All rabbits tolerated both types of implants well. After 3 months, exenterations were performed and the entire orbits were processed for HE staining. As shown in FIG. 9A and FIG. 9B, a thick capsule was observed to have formed around the plate of the AGV PF7 while nearly no capsule was observed around the microfluidic meshwork (brown). Average thickness of the fibrotic capsules beneath the AGV PF7 and the microfluidic meshworks were 89±6.6 µm and 1.3±0.6 µm, respectively. There was a significant difference between about the two groups (P=0.002, FIG. 10A through FIG. 10D).

Figure 11:
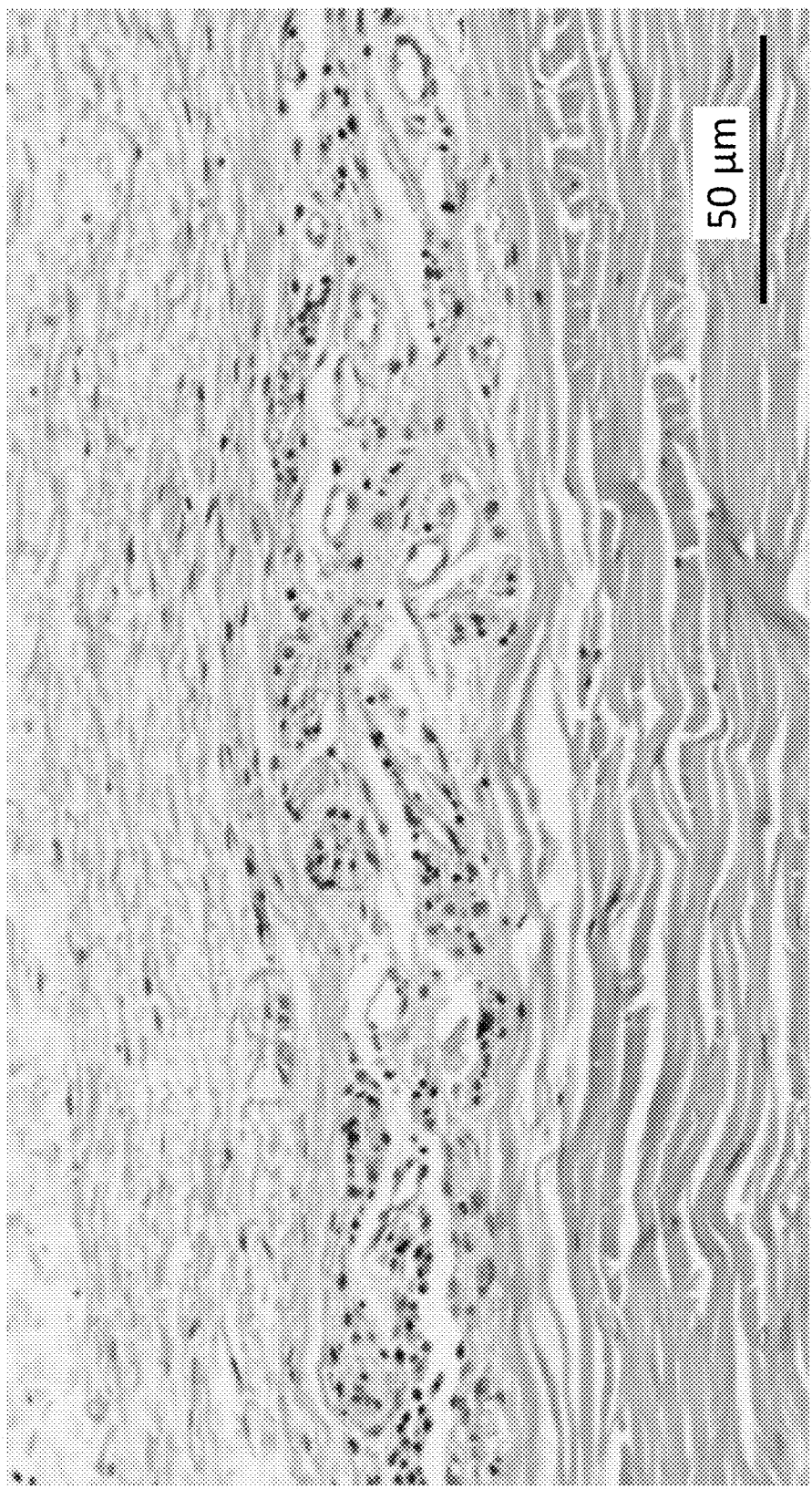
FIG. 11 depicts the histological study of tissue reaction to the stacked microfluidic meshwork. In the region where the meshwork has stacked into multiple layers during surgery, increased inflammatory reaction was noticed compared to the single layer region.

During further inspection of all the histological slides of meshwork implants, some inflammatory cells were observed to have accumulated in the region where the meshwork had stacked into multiple layers during surgery (<10% of the total area, FIG. 11). This was not observed around monolayer meshwork.

Presented herein is a modified concept of a GDI, in which the traditional plate of the GDI would be replaced by microfluidic meshwork. In this study, the tested hypothesis was that a properly designed meshwork can significantly suppress fibrotic tissue formation. In clear contrast to conventional implants, the microfluidic meshwork demonstrated excellent biocompatibility, evidenced by nearly no scar tissue and minimal inflammation.

Scar formation is the key obstacle in the surgical management of glaucoma. Modifications to the surgical technique as well as addition of intraoperative and postoperative medications have been studied in an effort to modulate fibrosis and promote long-term success with variable results (Alvarado J A et al., American journal of ophthalmology 146.2 (2008): 276-284; Costa V P et al., Ophthalmology 111.6 (2004): 1071-1076; Yazdani S et al., Journal of glaucoma 25.5 (2016): 415-421; Pakravan M et al., Ophthalmology 121.9 (2014): 1693-1698; Law S K et al., Ophthalmology 112.9 (2005): 1514-1520; Kurnaz E et al., European journal of ophthalmology 15.1 (2005): 27-31; Susanna R, Investigative Ophthalmology & Visual Science 44.13 (2003): 1181-1181; Teixeira S H et al., Journal of glaucoma 21.5 (2012): 342-348; Turalba A V et al., Clinical ophthalmology (Auckland, N Z) 8 (2014): 1311). Mitomycin-C and 5-fluorouracil have been used intraoperatively and postoperatively to reduce inflammation (Alvarado J A et al., American journal of ophthalmology 146.2 (2008): 276-284). However, the use of these agents has been associated with significant complications (Costa V P et al., Ophthalmology 111.6 (2004): 1071-1076; Yazdani S et al., Journal of glaucoma 25.5 (2016): 415-421). While corticosteroids offer reduced side effects, they are less potent and fail to provide significant improvement in long-term IOP reduction (Teixeira S H et al., Journal of glaucoma 21.5 (2012): 342-348). Modifications to the material comprising glaucoma surgical devices have also been explored. Studies that compared conventional silicone flexible GDI with polypropylene rigid GDI have shown a lower rate of encapsulation and higher success rates with the flexible plate (Hinkle D M et al., European journal of ophthalmology 17.5 (2007): 696-701). Several novel designs of glaucoma surgical devices aimed at reducing scar formation have been tested, including a MMC-coated valve, Ferrofluid valve, expanded polytetrafluoroethylene enclosed Ahmed, and Ahmed Glaucoma Valve with Adjunctive Amniotic Membrane (Sahiner N et al., Archives of Ophthalmology 127.4 (2009): 448-453; Paschalis E I et al., PLoS one 8.6 (2013): e67404; DeCroos F C et al., Current eye research 34.7 (2009): 562-567; Lee J W et al., Ophthalmic research 51.3 (2014): 129-139). These modifications and designs have been shown to decrease the amount of fibrosis and scar tissue when compared to conventional glaucoma devices but still resulted in significant capsule formation (DeCroos F C et al., Current eye research 34.7 (2009): 562-567; Lee J W et al., Ophthalmic research 51.3 (2014): 129-139).

The most active phase of capsule formation occurs in the 3 months following implantation (Thieme H et al., Journal of glaucoma 20.4 (2011): 246-251). Although many theories have been proposed to explain the increased rate of encapsulation with glaucoma surgical devices, including those on the physical profile of the implant (e.g. size and material) and fibrosis stimulation through early exposure to inflammatory mediators, the fundamental mechanisms of these tissue reactions are not clearly understood (Hinkle D M et al., European journal of ophthalmology 17.5 (2007): 696-701; Nouri-Mandavi K et al., American journal of ophthalmology 136.6 (2003): 1001-1008; Gedde S J et al., Current opinion in ophthalmology 24.2 (2013): 87-95). Nonetheless, in a series of recent works, neural probes were successfully engineered to suppress tissue reactions by addressing two important problems (Liu J et al., Nature nanotechnology 10.7 (2015): 629-636). First, the mechanical mismatch between about the tissue and the implant gives rise to interfacial forces that constantly elicit tissue reactions. Second, the presence of the solid implant interrupts the cellular and vascular networks at the implant site (Anderson J M et al., Seminars in immunology. Vol. 20. No. 2. Academic Press, 2008). In order to achieve optimal biocompatibility, these two issues must be addressed through substantial changes to the implant's mechanical properties and geometric structure. Hence, the implant was designed as a network of ultra-flexible interconnected cellular-sized channels in order to optimize its fluidic conductance while introducing minimum perturbation to the cellular and vascular processes at the implant site.

Additionally, during the histological examination of the dissected specimens, some inflammatory cell activation was observed at the edge of the meshwork implant wherever the meshwork was folded or stacked into layers during the surgery. These regions were less than 10% of the total meshwork area. It was postulated that when the meshwork was folded into multiple layers, its flexibility and hence its biocompatibility with eye tissue was compromised. This led to increased inflammatory cell activation and aggregation. This was not noticed in the majority of the areas where a single layer was maintained.

A New Zealand rabbit model was chosen for this study because this model has been previously used to study the effects of various biomaterials as well as newly-designed glaucoma surgical devices on the degree of fibrosis (Ayyala R S et al., Archives of Ophthalmology 117.2 (1999): 233-236; Ayyala R S et al., Archives of Ophthalmology 118.8 (2000): 1081-1084). Subsequent clinical studies were concordant and confirmed the applicability of the rabbit model (Law S K et al., Ophthalmology 112.9 (2005): 1514-1520; Ishida K et al., Ophthalmology 113.8 (2006): 1320-1326). The plate of AGV FP7, one of the most commonly used glaucoma surgical device in practice, was chosen as the control group. In addition to its popularity, AGV FP7 has been well characterized in the rabbit model and a large amount of published histological results can serve as reference. In the present study, the average capsule thickness under the AGV PF7 plate implant was 89 µm, which is comparable with the capsule thickness reported in the literature (Sahiner N et al., Archives of Ophthalmology 127.4 (2009): 448-453; Paschalis E I et al., PLoS one 8.6 (2013): e67404; DeCroos F C et al., Current eye research 34.7 (2009): 562-567; Lee J W et al., Ophthalmic research 51.3 (2014): 129-139).

The mechanical mismatch between about tissue and implant may not be the only factor affecting fibrosis. It is known that inflamed AH may also lead to inflammation around the implant and elicit tissue reactions (Kim Y G et al., Journal of glaucoma 18.6 (2009): 443-447). While the present study did not account for this, the results show that the AGV PF7 plate had a significant amount of fibrotic capsule even without AH flow. This suggests that the implant itself is one of the major, if not the total, cause of fibrosis. Furthermore, inflamed AH can be treated with extensive anti-inflammatory medication, such as steroid eye drops and/or anti-aqueous suppressants to minimize the effect.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An implant device for reducing intraocular pressure, comprising:
    a plurality of longitudinal microchannels each having a tubular structure with a lumen running throughout;
    a plurality of lateral microchannels each having a tubular structure with a lumen running throughout; and
    a plurality of fluid outlets positioned on at least a portion of the longitudinal microchannels and lateral microchannels;
    wherein the plurality of lateral microchannels at least partially intersect the plurality of longitudinal microchannels to form a flexible grid-like mesh including a plurality of open spaces formed between the plurality of longitudinal and lateral microchannels;
    wherein the lumen of the plurality of lateral microchannels are in fluid connection with the lumen of the plurality of longitudinal microchannels; and
    wherein at least a portion of the fluid outlets are positioned on a plurality of branches comprising short lengths of microchannel tubes including a free end positioned within the open spaces of the mesh and fluidly connected to the longitudinal microchannels, the lateral microchannels, or both.

2. The device of claim 1, wherein the longitudinal microchannels and the lateral microchannels have diameters between about 1 and 100 µm.

3. The device of claim 1, wherein the plurality of longitudinal microchannels are spaced between about 10 and 1000 µm apart and the plurality of lateral microchannels are spaced between about 10 and 1000 µm apart.

4. The device of claim 1, wherein the longitudinal microchannels and the lateral microchannels have diameters between about 10 and 20 µm the plurality of longitudinal microchannels are spaced between about 100 and 200 µm apart, and the plurality of lateral microchannels are spaced between about 100 and 200 µm apart.

5. The device of claim 1, wherein the longitudinal microchannels and the lateral microchannels have wall thicknesses between about 10 and 1000 nm.

6. The device of claim 1, wherein the grid-like mesh has a substantially planar size of between about 50 and 500 mm$^2$.

7. The device of claim 1, wherein two or more grid-like meshes are stacked on top of each other and fluidly interconnected by a plurality of vertical microchannels to form a 3D mesh, each vertical microchannel having a tubular structure with a lumen running throughout.

8. The device of claim 7, wherein the 3D mesh comprises longitudinal microchannels, lateral microchannels, and vertical microchannels having substantially similar dimensions and spacing.

9. The device of claim 7, wherein the 3D mesh comprises longitudinal microchannels, lateral microchannels, and vertical microchannels having variable dimensions and spacing.

10. The device of claim 9, wherein the 3D mesh comprises an inner region surrounded by an outer region, wherein the inner region comprises fluidly interconnected microchannels with diameters between about 40 and 60 µm and the outer region comprises fluidly interconnected microchannels with diameters between about 10 µm and 20 µm.

11. The device of claim 1, wherein the grid-like mesh further comprises an interface fluidly connectable to a drainage tube.

12. The device of claim 11, wherein the drainage tube comprises a pressure-sensitive valve selected from the group consisting of: a duckbill valve, a joker valve, a flapper valve, a reed valve, and a leaf valve.

13. The device of claim 12, wherein the pressure-sensitive valve is configured to permit drainage of fluid above an intraocular pressure of between about 8 and 10 mmHg.

14. The device of claim 1, wherein the longitudinal microchannels and the lateral microchannels are at least partially porous and permeable to fluids and molecules.

15. The device of claim 1, wherein the plurality of longitudinal microchannels are substantially orthogonal to the plurality of lateral microchannels.

16. The device of claim 1, wherein the longitudinal microchannels and the lateral microchannels are constructed from a material selected from the group consisting of: SU-8 photoresist, parylene, polyimide, polytetrafluoroethylene (PTFE), silicon oxides, silicon nitride, silicon carbide, and aluminum oxides.

17. A method of managing intraocular pressure, comprising the steps of:
    providing the implant device of claim 1 connected to a drainage tube;
    breaching the conjunctiva of an eye to access the sclera;
    placing the implant device against the sclera of the eye without sutures;
    forming a hole in the limbus of the eye adjacent to the implant device, the hole having access to the anterior or posterior chamber of the eye;
    threading the drainage tube through the hole; and
    closing the conjunctiva.

18. A method of managing intraocular pressure, comprising the steps of:
    providing the implant device of claim 1;
    rolling the implant device into an elongate tubular shape;
    loading the implant device into a hollow syringe tip;
    piercing the conjunctiva of the eye with the syringe tip; and
    injecting the implant device into the eye such that the implant device bridges the subconjunctival space and the anterior or posterior chamber of the eye.

19. The method of claim 18, wherein the implant device is implanted in fluid connection with a drainage tube positioned in the anterior or posterior chamber of the eye, the drainage tube having a pressure-sensitive valve.

* * * * *